(12) United States Patent
Benbow et al.

(10) Patent No.: US 7,671,072 B2
(45) Date of Patent: Mar. 2, 2010

(54) AMINOPYRAZOLE DERIVATIVES AS GSK-3 INHIBITORS

(75) Inventors: John W. Benbow, Norwich, CT (US); Daniel W. Kung, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/580,615

(22) PCT Filed: Nov. 15, 2004

(86) PCT No.: PCT/IB2004/003749

§ 371 (c)(1), (2), (4) Date: May 23, 2007

(87) PCT Pub. No.: WO2005/051919

PCT Pub. Date: Jun. 9, 2005

(65) Prior Publication Data

US 2007/0276010 A1 Nov. 29, 2007

Related U.S. Application Data

(60) Provisional application No. 60/525,436, filed on Nov. 26, 2003.

(51) Int. Cl.
- A61K 31/4155 (2006.01)
- A61K 31/435 (2006.01)
- C07D 401/02 (2006.01)
- C07D 231/10 (2006.01)

(52) U.S. Cl. .................... 514/341; 514/406; 546/275.4; 548/371.4; 548/373.1

(58) Field of Classification Search .............. 548/371.4, 548/373.1; 546/275.4; 514/341, 406
See application file for complete search history.

(56) References Cited

U.S. PATENT DOCUMENTS

| | | | |
|---|---|---|---|
| 3,819,706 A | 6/1974 | Mehta | |
| 3,885,046 A | 5/1975 | Mehta | |
| 4,007,196 A | 2/1977 | Christensen et al. | |
| 4,085,225 A | 4/1978 | Welle et al. | |
| 4,314,081 A | 2/1982 | Molloy et al. | |
| 4,338,317 A | 7/1982 | Temple, Jr. et al. | |
| 4,423,049 A | 12/1983 | Temple, Jr. | |
| 4,535,186 A | 8/1985 | Husbands et al. | |
| 4,536,518 A | 8/1985 | Welch, Jr. et al. | |
| 4,690,931 A | 9/1987 | Wick et al. | |
| 4,804,663 A | 2/1989 | Kennis et al. | |
| 4,833,142 A | 5/1989 | Hartog et al. | |
| 4,895,841 A | 1/1990 | Sugimoto et al. | |
| 4,948,807 A | 8/1990 | Rosin et al. | |
| 5,122,525 A | 6/1992 | Bright et al. | |
| 5,162,339 A | 11/1992 | Lowe, III | |
| 5,185,343 A | 2/1993 | Chenard | |
| 5,229,382 A | 7/1993 | Chakrabarti et al. | |
| 5,232,929 A | 8/1993 | Desai et al. | |
| 5,240,958 A | 8/1993 | Campion et al. |
| 5,272,160 A | 12/1993 | Chenard |
| 5,310,763 A | 5/1994 | Campion et al. |
| 5,312,925 A | 5/1994 | Allen et al. |
| 5,332,817 A | 7/1994 | Desai et al. |
| 5,356,905 A | 10/1994 | Butler |
| 5,358,948 A | 10/1994 | Bradshaw |
| 5,373,018 A | 12/1994 | Cugola et al. |
| 5,455,258 A | 10/1995 | MacPherson et al. |
| 5,466,823 A | 11/1995 | Talley et al. |
| 5,474,995 A | 12/1995 | Ducharme et al. |
| 5,506,242 A | 4/1996 | MacPherson et al. |
| 5,510,350 A | 4/1996 | Oxford et al. |
| 5,530,161 A | 6/1996 | Campion et al. |
| 5,538,984 A | 7/1996 | Villalobos et al. |
| 5,552,419 A | 9/1996 | MacPherson et al. |
| 5,587,458 A | 12/1996 | King et al. |
| 5,602,169 A | 2/1997 | Hewawasam et al. |
| 5,633,272 A | 5/1997 | Talley et al. |
| 5,672,615 A | 9/1997 | MacPherson et al. |
| 5,679,683 A | 10/1997 | Bridges et al. |
| 5,703,240 A | 12/1997 | Armour et al. |

(Continued)

FOREIGN PATENT DOCUMENTS

WO     WO 94/21619     9/1994

(Continued)

OTHER PUBLICATIONS

Stella, Valentino J, Expert Opinion of Therapeutic Patents, Prodrugs as therapeutics, 2004 14(3): 277-280.*

(Continued)

*Primary Examiner*—Kamal A Saeed
*Assistant Examiner*—Samantha L Shterengarts
(74) *Attorney, Agent, or Firm*—Gregg C. Benson; John A. Wichtowski

(57) ABSTRACT

The present invention provides compounds of formula (I) the stereoisomers and prodrugs thereof, and the pharmaceutically acceptable salts of the compounds, stereoisomers, and prodrugs, wherein $R^1$, $R^2$, and $R^3$ are as defined herein; pharmaceutical compositions thereof; combinations thereof; and uses thereof in the treatment of, inter alia, conditions, diseases, and symptoms including, inter alia, Alzheimer's Disease, cancer, dementia, depression, diabetes, hair loss, schizophrenia, and stroke.

(I)

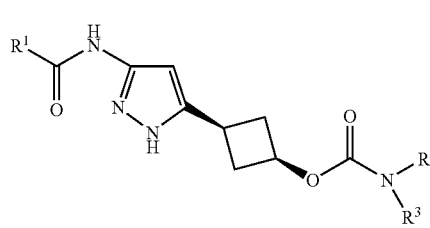

7 Claims, No Drawings

U.S. PATENT DOCUMENTS

| | | |
|---|---|---|
| 5,716,965 A | 2/1998 | Ito et al. |
| 5,719,147 A | 2/1998 | Dorn et al. |
| 5,744,480 A | 4/1998 | Lowel, II et al. |
| 5,744,483 A | 4/1998 | Butler et al. |
| 5,747,498 A | 5/1998 | Schnur et al. |
| 5,763,699 A | 6/1998 | German et al. |
| 5,773,450 A | 6/1998 | Lowe, III et al. |
| 5,792,783 A | 8/1998 | Tang et al. |
| 5,807,867 A | 9/1998 | Ito et al. |
| 5,834,504 A | 11/1998 | Tang et al. |
| 5,843,966 A | 12/1998 | Armour et al. |
| 5,851,999 A | 12/1998 | Ullrich et al. |
| 5,852,038 A | 12/1998 | Ito et al. |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,009 A | 3/1999 | Ito et al. |
| 5,886,020 A | 3/1999 | Tang et al. |
| 5,932,595 A | 8/1999 | Bender et al. |
| 5,939,433 A | 8/1999 | Ito et al. |
| 5,962,472 A | 10/1999 | Bourson et al. |
| 5,994,351 A | 11/1999 | Robinson et al. |
| 6,046,213 A | 4/2000 | Chenard et al. |
| 6,051,593 A | 4/2000 | Tang et al. |
| 6,077,864 A | 6/2000 | Burgess et al. |
| 6,087,392 A | 7/2000 | Reiter |
| 6,090,852 A | 7/2000 | Dack et al. |
| 6,110,964 A | 8/2000 | Robinson |
| 6,114,371 A | 9/2000 | Tang et al. |
| 6,124,317 A | 9/2000 | Bigge et al. |
| 6,124,323 A | 9/2000 | Bigge et al. |
| 6,130,234 A | 10/2000 | Bigge et al. |
| 6,133,305 A | 10/2000 | Tang et al. |
| 6,147,061 A | 11/2000 | Reiter |
| 6,147,074 A | 11/2000 | Robinson et al. |
| 6,162,804 A | 12/2000 | Bilodeau et al. |
| 6,174,889 B1 | 1/2001 | Cockerill et al. |
| 6,207,669 B1 | 3/2001 | Cockerill et al. |
| 6,218,404 B1 | 4/2001 | Bigge et al. |
| 6,235,741 B1 | 5/2001 | Bilodeau et al. |
| 6,291,455 B1 | 9/2001 | Thomas et al. |
| 6,294,532 B1 | 9/2001 | Thomas et al. |
| 6,303,636 B1 | 10/2001 | Robinson et al. |
| 6,310,238 B1 | 10/2001 | Sezi et al. |
| 6,333,036 B1 | 12/2001 | Arminjon et al. |
| 6,380,186 B1 | 4/2002 | Howard |
| 6,380,203 B1 | 4/2002 | Bilodeau et al. |
| 6,380,219 B1 | 4/2002 | Robinson et al. |
| 6,391,874 B1 | 5/2002 | Cockerill et al. |
| 6,395,734 B1 | 5/2002 | Tang et al. |
| 6,403,592 B1 | 6/2002 | Howard |
| 6,423,708 B1 | 7/2002 | Gibbs et al. |
| 6,448,270 B1 | 9/2002 | Bigge et al. |
| 6,462,048 B2 | 10/2002 | Howard |

FOREIGN PATENT DOCUMENTS

| | | |
|---|---|---|
| WO | WO 97/13760 | 4/1997 |
| WO | WO 97/23202 | 7/1997 |
| WO | WO 98/14451 | 4/1998 |
| WO | WO 98/18793 | 5/1998 |
| WO | WO 98/34915 | 8/1998 |
| WO | WO 98/34918 | 8/1998 |
| WO | WO 99/24440 | 5/1999 |
| WO | WO 99/35132 | 7/1999 |
| WO | WO 99/35146 | 7/1999 |
| WO | WO 02/18346 | 3/2002 |

OTHER PUBLICATIONS

Wolff et al. (Burger's Medicinal Chemistry, 5th Ed., vol. 1, pp. 975-977, 1994).*

Testa, Bernard, Biochemical Pharmacology, Prodrug Research: futile or fertile? 68 (2004) 2097-2106.*

Ettmayer, Peter, Medicinal Chemistry, Lessons Learned from Marketed and Investigational Prodrugs, 47(10) (2004) 2394-2404.*

US 6,387,931, (withdrawn).

Ali, A., et al., "Glycogen Synthase Kinase-3: Properties, Functions, and Regulation," *Chem. Rev.*, 2001, 2527-2540, vol. 101.

Baar, K., et al., "Phosphorylation Of $p70^{S6k}$ Correlates With Increased Skeletal Muscle Mass Following Resistance Exercise," *Am. J. Physiol.*, 1999, C120-C127, vol. 276.

Badorff, C., et al., "Fas Receptor Signaling Inhibits Glycogen Synthase Kinase 3β And Induces Cardiac Hypertrophy Following Pressure Overload," *The Journal Of Clinical Investigation*, 2002, 373-381, vol. 109, No. 3.

Barnes, P., "Cytokine Modulators As Novel Therapies For Asthma," *Ann. Rev. Pharmacol. Toxicol.*, 2002, 81-98, vol. 42.

Beals, C., et al., "Nuclear Export of NF-ATc Enhanced By Glycogen Synthase Kinase-3," *Science*, 1997, 1930-1933, vol. 275.

Berge, S., et al., "Pharmaceutical Salts," *Journal of Pharmaceutical Science*, 1977, 1-19, vol. 66, No. 1.

Brunn, G., et al., "Phosphorylation Of The Translational Repressor PHAS-I By The Mamalian Target Of Rapamycin," *Science*, 1997, 99-101, vol. 277.

Castro A., et al., "Inhibition Of Tau Phosphorylation: A New Therapeutic Strategy For The Treatment Of Alzheimer's Disease And Other Neurodegenerative Disorders," *Expert Opinion On Therapeutic Patents*, 2000, 1519-1527, vol. 10, No. 10.

Cohen, P., "The Role Of Protein Phosphorylation In Human Health And Disease Delivered On Jun. $30^{th}$ 2001 At the FEBS Meeting In Lisbon," *Eur. J. Biochem.*, 2001, 5001-5010, vol. 268.

Cross, D., et al.,"Selective Small-Molecule Inhibitors Of Glycogen Synthase Kinase-3 Activity Protect Primary Neurones From Death," *Journal of Neurochemistry*, 2001, 94-102, vol. 77.

Eastman, Q., et al., "Regulation Of LEF-1/TCF Transcription Factors By Wnt And Other Signals," *Current Opinion In Cell Biology*, 1999, 233-240, vol. 11.

Eldar-Finkelman, H., "Glycogen Synthase Kinase 3: an Emerging Therapeutic Target," *Trends In Molecular Medicine*, 2002, 126-132, vol. 8, No. 3.

Embi, N., et al., "Glycogen Synthase Kinase-3 From Rabbit Skeletal Muscle," *Euro. J. Bicochem*, 1980, 519-527, vol. 107.

Fuchs, E., et at., "At The Roots Of A Never-Ending Cycle," *Developmental Cell*, 2001, 13-25, vol. 1.

Grimes, C., et al., "The Multifaceted Roles Of Glycogen Synthase Kinase 3β In Cellular Signaling," *Progress In Neurobiology*, 2001, 391-426, vol. 65.

Haq, S., et al., "Glycogen Synthase Kinase-3β Is A Negative Reulator Of Cardiomyocyte Hypertrophy," *The Journal Of Cell Biology*, 2000, 117-129, vol. 151, No. 1.

Kim, L., et al., "GSK3, A Master Switch Regulating Cell-Fate Specification and Tumorigenesis," Current Opinion In Genetics & Development, 2000, 508-514, vol. 10.

Klein, P., et al., "A Molecular Mechanism For The Effect Of Lithium On Development," *Proc. Natl. Acad. Sci.* USA, 1996, 8455-8459, vol. 93.

Lau, K., et al., "Expression Analysis Of Glycogen Synthase Kinase-3 In Human Tissues," *J. Peptide Res.*, 1999, 85-91, vol. 54.

Meijer, L., et al., "Properties And Potential Applications Of Chemical Inhibitors Of Cyclin-Dependent Kinases," *Pharmacol. And Ther.*, 1999, 279-284, vol. 82, Nos. 2-3.

Millar, S., et al., "WNT Signaling In The Control Of Hair Growth And Structure," *Developmental Biology*, 1999, 133-149, vol. 207.

Nikoulina, S., et al., "Inhibition Of Glycogen Synthase Kinase 3 Improves Insulin Action And Glucose Metabolism In Human Skeletal Muscle," *Diabetes*, 2002, 2190-2198, vol. 51.

Orena, S., et al., "Inhibition Of Glycogen-Synthase Kinase 3 Stimulates Glycogen Synthase And Glucose Transport By Distinct Mechanisms In 3T3-L1 Adipocytes," *The Journal of Biological Chemistry*, 2000, 15765-15772, vol. 275, No. 21.

Regan, J., et al., "Pyrazole Urea-Based Inhibitors Of p38 MAP Kinase: From Lead Compound To Clinical Candidate," *J. Med. Chem.*, 2002, 2994-3008, vol. 45.

Rhoads, R., et al., "Signal Transduction Pathways That Regulate Eukaryotic Protein Synthesis," *The Journal Of Biological Chemistry*, 1999, 30337-30340, vol. 274, No. 43.

Sasaki, C., et al., "Different Expression Of Glycogen Synthase Kinase-3β Between Young And Old Rat Brains After Transient Middle Cerebral Artery Occlusion," *Neurological Research*, 2001, 588-592, vol. 23.

Sausville, E., et al., "Cyclin-Dependent Kinases: Initial Approaches To Explloit a Novel Therapeutic Target," *Pharmacol. And Ther.*, 1999, 285-292, vol. 82, Nos. 2-3.

Summers, S., et al., "The Role of Glyocgen Synthase Kinase 3β In Insulin-Stimulated Glucose Metabolism," *The Journal of Biological Chemistry*, 1999, 17934-17940, vol. 274, No. 25.

Tong, H., "Phosphorylation Of Glycogen Synthase Kinase-3β During Preconditioning Through A Phosphatidylinositol-3-Kinase-Dependent Pathway Is Cardioprotective," et al., *Circulation Research*, 2002, 377-379, vol. 90.

Vijayaraghavan, S., et al., "Sperm Motility Development In The Epididymis Is Associated With Decreased Glycogen Synthase Kinase-3 And Protein Phosphatase 1 Activity," *Biology Of Reproduction*, 1996, 709-718, vol. 54.

Vyas, D., et al., "GSK-3β Negatively Regulates Skeletal Myotube Hypertrophy," *Am. J. Physiol. Cell Physiol.*, 2002, C545-C551, vol. 283.

Williams, R., et al., "Lithium Therapy And Signal Transduction," *TIPS*, 2000, 61-64, vol. 21.

Woodgett, J., "Molecular Cloning And Expression Of Glycogen Synthase Kinase-3/Factor A," *The EMBO Journal*, 1990, 2431-2438, vol. 9, No. 8.

\* cited by examiner

AMINOPYRAZOLE DERIVATIVES AS GSK-3 INHIBITORS

FIELD OF THE INVENTION

The invention relates to certain 5-cyclobutyl-3-aminopyrazoles which inhibit kinases, such as glycogen synthase kinase-3 (GSK-3), cyclin-dependent kinase-2 (cdk-2), and cyclin-dependent kinase-5 (cdk-5). As such, the compounds are useful in the treatment of conditions, diseases, and symptoms including, inter alia, Alzheimer's Disease, cancer, dementia, depression, diabetes, hair loss, schizophrenia, and stroke.

BACKGROUND OF THE INVENTION

The serine/threonine kinase cdk-2 is essential for normal cellular cycling and plays a critical role in disorders arising from abnormal cell cycling, a common characteristic of many oncological disorders. Inhibitors of cdk-2 are therefore useful in the treatment of various types of cancers and other diseases or conditions related to abnormal cell growth. See, for example, Meijer, et al., Pharmacol. and Therapeutics, 82 (2-3), 279-284 (1999), Sausville, et al., Pharmacol. and Therapeutics, 82 (2-3), 285-292 (1999). The serine/threonine kinase cdk-5, along with its cofactor p25, or the longer cofactor p35, has been linked to neurodegenerative disorders, and inhibitors of cdk-5 are therefore useful in the treatment of disorders such as Alzheimer's Disease, Parkinson's Disease, stroke, and Huntington's Disease. Treatment of such neurodegenerative disorders using cdk-5 inhibitors is supported by the finding that cdk-5 is involved in the phosphorylation of tau protein, and dopamine and cyclic AMP-regulated phosphoprotein (DARPP-32) at threonine 75, and is thus indicated as playing a role in dopaminergic transmission.

Glycogen synthase kinase-3 (GSK-3), a proline-directed, serine/threonine kinase for which two isoforms, GSK-3α and GSK-3β, have been identified, phosphorylates the rate-limiting enzyme of glycogen synthesis, glycogen synthase (GS). See, for example, Embi, et al., Eur. J. Biochem., 107, 519-527 (1980). GSK-3α and GSK-3β are both highly expressed in the body. See, for example, Woodgett, et al., EMBO, 9, 2431-2438 (1990) and Loy, et al., J. Peptide Res., 54, 85-91 (1999). Besides GS, a number of other GSK-3 substrates have been identified, including many metabolic, signaling, and structural proteins. Notable among the plurality of signaling proteins regulated by GSK-3 are many transcription factors, including activator protein-1; cyclic AMP response element binding protein (CREB); the nuclear factor (NF) of activated T-cells; heat shock factor-1; β-catenin; c-Jun; c-Myc; c-Myb; and NF-$_{KB}$. See, for example, C. A. Grimes, et al., Prog. Neurobiol., 65, 391-426 (2001), H. Eldar-Finkelman, Trends in Molecular Medicine, 8, 126-132 (2002), and P. Cohen, et al., Nature, 2, 1-8, (2001). Accordingly, targeting the activity of GSK-3 has significant therapeutic potential in the treatment of many disparate pathologies and conditions, for example, Alzheimer's Disease (A. Castro, et al., Exp. Opin. Ther. Pat., 10, 1519-1527 (2000)); asthma (P. J. Barnes, Ann. Rev. Pharmacol. Toxicol., 42, 81-98 (2002)); cancer (Beals, et al., Science, 275, 1930-1933 (1997), L. Kim, et al., Curr. Opin. Genet. Dev., 10, 508-514 (2000), and Q. Eastman, et al., Curr. Opin. Cell Biol., 11, 233 (1999)); diabetes and its related sequelae, for example, Syndrome X and obesity (S. E. Nikoulina, et al., Diabetes, 51, 2190-2198 (2002), Orena, et al., JBC, 15765-15772 (2000), and Summers, et al., J. Biol. Chem., 274, 17934-17940 (1999)); hair loss (S. E. Millar, et al., Dev. Biol., 207, 133-149 (1999) and E. Fuchs, et al., Dev. Cell, 1, 13-25 (2001)); inflammation (P. Cohen, Eur. J. Biochem., 268, 5001-5010 (2001)); mood disorders, such as depression (A. Adnan, et al., Chem. Rev., 101, 2527-2540 (2001) and R. S. B. Williams, et al., Trends Phamacol. Sci., 21, 61-64 (2000)); neuronal cell death and stroke (D. A. E. Cross, et al., J. Neurochem., 77, 94-102 (2001) and C. Sasaki, et al., Neurol. Res., 23, 588-592 (2001)); bipolar disorder (Klein, et al., PNAS, 93, 8455-8459 (1996)); skeletal muscle atrophy (G. J. Brunn, et al., Science, 277, 99-101 (1997), R. E. Rhoads, J. Biol. Chem., 274, 30337-30340 (1999), V. R. Dharmesh, et al., Am. J. Physiol. Cell Physiol. 283, C545-551 (2002), and K. Baar, et al., A. J. Physiol., 276, C120-C127 (1999)); decreased sperm motility (Vijayaraghavan, et al., Biol. Reproduction, 54, 709-718 (1996)); and in cardio-protection (C. Badorff, et al., J. Clin. Invest., 109, 373-381 (2002), S. Haq, et al., J. Cell Biol., 151, 117-129 (2000), and H. Tong, et al., Circulation Res., 90, 377-379 (2002)).

Certain pyrazole derivatives of formula (II),

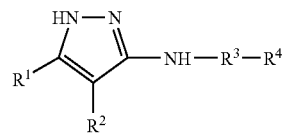

(II)

useful as inhibitors of cdk2, cdk5, and GSK-3, are disclosed in commonly-assigned PCT International Application Publication No. WO 02/18346, wherein $R^1$, $R^2$, $R^3$, and $R^4$ are as defined therein.

SUMMARY OF THE INVENTION

The present invention provides compounds of formula (I)

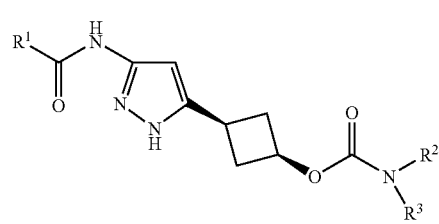

(I)

the stereoisomers and prodrugs thereof, and the pharmaceutically acceptable salts of the compounds, stereoisomers, and prodrugs, wherein $R^1$, $R^2$, and $R^3$ are as defined herein; pharmaceutical compositions thereof; combinations thereof; and uses thereof in the treatment of, inter alia, conditions, diseases, and symptoms including, inter alia, Alzheimer's Disease, cancer, dementia, depression, diabetes, hair loss, schizophrenia, and stroke.

DETAILED DESCRIPTION OF THE INVENTION

The invention provides compounds of formula (I)

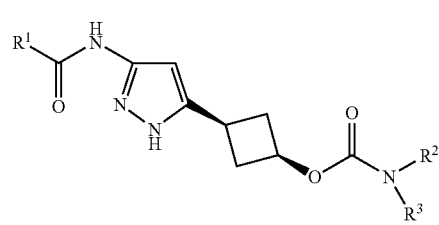

(I)

the stereoisomers and prodrugs thereof, and the pharmaceutically acceptable salts of the compounds, stereoisomers, and prodrugs, wherein:

$R^1$ is:

(A) —$(C_1-C_6)$alkyl, optionally substituted independently with from one to three (a) halogen; (b) heteroaryl, optionally substituted independently with from one to three —$(C_1-C_6)$alkyl; trifluoromethyl; or —$(C_1-C_6)$alkoxy; (c) aryl, optionally substituted independently with from one to three halogen; —$(C_1-C_6)$alkoxy; trifluoromethyl; —$(C_1-C_6)$alkyl; or —$C(O)(C_1-C_6)$alkyl; (d) —$OR^5$; (e) —$(C_3-C_8)$cycloalkyl; or (f) heterocycloalkyl;

(B) —$(C_3-C_8)$cycloalkyl, optionally substituted independently with from one to three (g) heteroaryl, optionally substituted independently with from one to three —$(C_1-C_6)$alkyl; trifluoromethyl; or —$(C_1-C_6)$alkoxy; (h) aryl, optionally substituted independently with from one to three halogen; —$(C_1-C_6)$alkoxy; trifluoromethyl; —$(C_1-C_6)$alkyl; or —$C(O)(C_1-C_6)$alkyl; (i) heterocycloalkyl; (j) —$OR^5$; or (k) —$(C_1-C_6)$alkyl, optionally substituted with from one to three halogen;

(C) heterocycloalkyl, optionally substituted with from one to three (l) heteroaryl, optionally substituted independently with from one to three —$(C_1-C_6)$alkyl; trifluoromethyl; or —$(C_1-C_6)$alkoxy; (m) aryl, optionally substituted independently with from one to three halogen; —$(C_1-C_6)$alkoxy; trifluoromethyl; —$(C_1-C_6)$alkyl; or —$C(O)(C_1-C_6)$alkyl; (n) —$(C_3-C_8)$cycloalkyl; (o) heterocycloalkyl; (p) —$OR^5$; or (q) —$(C_1-C_6)$alkyl, optionally substituted with from one to three halogen; or (D) heteroaryl, optionally substituted with from one to three —$(C_1-C_6)$alkyl or trifluoromethyl;

$R^2$ and $R^3$ are, independently, (E) hydrogen;

(F) —$(C_1-C_6)$alkyl, optionally substituted independently with from one to three (r) halogen; (s) aryl, optionally substituted independently with from one to three halogen; trifluoromethyl; —$(C_1-C_6)$alkyl, or —$(C_1-C_6)$alkoxy, optionally substituted with from one to three fluorine atoms; (t) heteroaryl, optionally substituted independently with from one to three nitro; —$(C_1-C_6)$alkyl; trifluoromethyl; halogen; or —$(C_1-C_6)$alkoxy; (u) heterocycloalkyl, optionally substituted independently with one to three —$(C_1-C_6)$alkyl; oxo; aryl; or heteroaryl; (v) —$(C_3-C_8)$cycloalkyl, optionally substituted independently with from one to three cyano or aryl; (w) —$NHR^4$; (x) —$OR^5$; (y) —$N[(C_1-C_6)alkyl]_2$; or (z) cyano;

(G) —$(C_3-C_8)$cycloalkyl, optionally substituted independently with from one to three cyano or aryl;

(H) aryl, optionally substituted independently with from one to three halogen; —$(C_1-C_6)$alkoxy; trifluoromethyl; or —$(C_1-C_6)$alkyl;

(I) heteroaryl, optionally substituted independently with from one to three —$(C_1-C_6)$alkyl or —$(C_1-C_6)$alkoxy; or (J) heterocycloalkyl, optionally substituted with from one to three —$(C_1-C_6)$alkyl, optionally substituted with aryl; or $R^2$ and $R^3$, taken together with the nitrogen atom to which they are attached, form a heterocycloalkyl ring, optionally substituted independently with (aa) —$(C_1-C_6)$alkyl, optionally substituted with —$R^4$ or —$OR^5$; (bb) aryl; (cc) heteroaryl; (dd) —$N[(C_1-C_6)alkyl]R^4$; (ee) —$R^4$; or (ff) —$(C_1-C_6)$alkoxy;

$R^4$ is (K) —$(C_1-C_6)$alkyl; (L) —$C(O)(C_1-C_6)$alkyl; (M) —$C(O)O(C_1-C_6)$alkyl, optionally substituted with aryl; (N) aryl; (O) heteroaryl; or (P) heterocycloalkyl, wherein each (N) aryl, (O) heteroaryl, or (P) heterocycloalkyl group is optionally substituted independently with from one to three (gg) halogen; (hh) nitro; (ii) trifluoromethyl; (jj) —$(C_1-C_6)$alkyl; or (kk) —$N[(C_1-C_6)alkyl][C(O)(C_1-C_6)alkyl]$; and $R^5$ is (Q) —$(C_1-C_6)$alkyl; (R) —$C(O)(C_1-C_6)$alkyl; (S) aryl; (T) heteroaryl; or (U) heterocycloalkyl, wherein each (S) aryl, (T) heteroaryl, or (U) heterocycloalkyl group is optionally substituted independently with from one to three (ll) halogen; (mm) nitro; (nn) trifluoromethyl; (oo) —$(C_1-C_6)$alkyl; or (pp) —$N[(C_1-C_6)alkyl][C(O)(C_1-C_6)alkyl]$.

A generally preferred subgroup of the compounds of formula (I) comprises those compounds wherein:

$R^1$ is:

(A) —$(C_1-C_6)$alkyl, optionally substituted independently with (b) heteroaryl, optionally substituted independently with —$(C_1-C_6)$alkyl; trifluoromethyl; or —$(C_1-C_6)$alkoxy; (c) aryl, optionally substituted independently with from one to three halogen; —$(C_1-C_6)$alkoxy; trifluoromethyl; —$(C_1-C_6)$alkyl; (d) —$OR^5$; or (f) heterocycloalkyl;

(B) —$(C_3-C_8)$cycloalkyl, optionally substituted independently with (g) heteroaryl, optionally substituted independently with from one to three —$(C_1-C_6)$alkyl; trifluoromethyl; or —$(C_1-C_6)$alkoxy; (h) aryl, optionally substituted independently with from one to three halogen; —$(C_1-C_6)$alkoxy; trifluoromethyl; or —$(C_1-C_6)$alkyl; (i) heterocycloalkyl; (j) —$OR^5$; (k) —$(C_1-C_6)$alkyl, optionally substituted with from one to three halogen;

(C) heterocycloalkyl, optionally substituted with (l) heteroaryl, optionally substituted independently with from one to three —$(C_1-C_6)$alkyl; trifluoromethyl; or —$(C_1-C_6)$alkoxy; (m) aryl, optionally substituted independently with from one to three halogen; —$(C_1-C_6)$alkoxy; trifluoromethyl; —$(C_1-C_6)$alkyl; or —$C(O)(C_1-C_6)$alkyl; (n) —$(C_3-C_8)$cycloalkyl; (o) heterocycloalkyl; (p) —$OR^5$; or (q) —$(C_1-C_6)$alkyl, optionally substituted with from one to three halogen;

$R^2$ is hydrogen or —$(C_1-C_6)$alkyl;

$R^3$ is:

(F) —$(C_1-C_6)$alkyl, optionally substituted independently with from one to three (r) halogen; (s) aryl, optionally substituted independently with from one to three halogen; trifluoromethyl; —$(C_1-C_6)$alkyl, or —$(C_1-C_6)$alkoxy, optionally substituted with from one to three fluorine atoms; (t) heteroaryl, optionally substituted independently with from one to three —$(C_1-C_6)$alkyl; trifluoromethyl; halogen; or —$(C_1-C_6)$alkoxy; (u) heterocycloalkyl, optionally substituted independently with one to three —$(C_1-C_6)$alkyl; oxo; aryl; or heteroaryl; (v) —$(C_3-C_8)$cycloalkyl; (w) —$NHR^4$; (x) —$OR^5$; (y) —$N[(C_1-C_6)alkyl]_2$; or (z) cyano;

(G) —$(C_3-C_8)$cycloalkyl, optionally substituted independently with from one to three cyano or aryl; or (J) heterocycloalkyl, optionally substituted with from one to three —$(C_1-C_6)$alkyl, optionally substituted with aryl; or $R^2$ and $R^3$, taken together with the nitrogen atom to which they are attached, form a heterocycloalkyl ring, optionally substituted independently with (aa) —$(C_1-C_6)$alkyl, optionally substituted with —$R^4$ or —$OR^5$; (bb) aryl; (cc) heteroaryl; or (ff) —$(C_1-C_6)$alkoxy;

$R^4$ is (K) —$(C_1-C_6)$alkyl; (N) aryl; (O) heteroaryl; or (P) heterocycloalkyl, wherein each aryl, heteroaryl, or heterocycloalkyl group is optionally substituted independently with from one to three (gg) halogen; (ii) trifluoromethyl; or (jj) —$(C_1-C_6)$alkyl; and $R^5$ is (Q) —$(C_1-C_6)$alkyl; (S) aryl; (T) heteroaryl; or (U) heterocycloalkyl, wherein each (S) aryl, (T) heteroaryl, or (U) heterocycloalkyl group is optionally substituted independently with from one to three (ll) halogen; (nn) trifluoromethyl; or (oo) —$(C_1-C_6)$alkyl.

Another generally preferred subgroup of the compounds of formula (I) comprises those compounds wherein:

$R^1$ is:

(A) —$(C_1$-$C_6)$alkyl, optionally substituted independently with (b) heteroaryl, optionally substituted independently with —$(C_1$-$C_6)$alkyl or —$(C_1$-$C_6)$alkoxy; (c) aryl, optionally substituted independently with from one to three halogen; —$(C_1$-$C_6)$alkoxy; trifluoromethyl; or —$(C_1$-$C_6)$alkyl; or (d) —$OR^5$;

(B) —$(C_3$-$C_8)$cycloalkyl, optionally substituted independently with (g) heteroaryl, optionally substituted independently with from one to three —$(C_1$-$C_6)$alkyl or —$(C_1$-$C_6)$alkoxy; (h) aryl, optionally substituted independently with from one to three halogen; —$(C_1$-$C_6)$alkoxy; trifluoromethyl; or —$(C_1$-$C_6)$alkyl; (j) —$OR^5$; (k) —$(C_1$-$C_6)$alkyl, optionally substituted with from one to three halogen; or (C) heterocycloalkyl, optionally substituted with (l) heteroaryl, optionally substituted independently with from one to three —$(C_1*C_6)$alkyl or —$(C_1$-$C_6)$alkoxy; (m) aryl, optionally substituted independently with from one to three halogen; —$(C_1$-$C_6)$alkoxy; trifluoromethyl; or —$(C_1$-$C_6)$alkyl; (p) —$OR^5$; or (q) —$(C_1$-$C_6)$alkyl, optionally substituted with from one to three halogen;

$R^2$ is hydrogen or —$(C_1$-$C_6)$alkyl;

$R^3$ is:

(F) —$(C_1$-$C_6)$alkyl, optionally substituted independently with (s) aryl, optionally substituted independently with from one to three halogen; trifluoromethyl; —$(C_1$-$C_6)$alkyl, or —$(C_1$-$C_6)$alkoxy, optionally substituted with from one to three fluorine atoms; (t) heteroaryl, optionally substituted independently with from one to three —$(C_1$-$C_6)$alkyl or trifluoromethyl; and $R^5$ is (S) aryl, optionally substituted with halogen.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix "—$(C_a$-$C_b)$alkyl" indicates an alkyl moiety of the integer "a" to "b" carbon atoms, inclusive.

The term "alkoxy" denotes straight or branched, monovalent, saturated aliphatic chains of carbon atoms bonded to an oxygen atom, wherein the alkoxy group optionally incorporates one or more double or triple bonds, or a combination of double bonds and triple bonds. Examples of alkoxy groups include methoxy, ethoxy, propoxy, butoxy, isobutoxy, tert-butoxy, and the like.

The term "alkyl" denotes straight, or branched, monovalent chains of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, and the like.

The term "aryl" denotes a monocyclic, or polycyclic, aromatic hydrocarbon. Examples of aryl groups include anthracenyl, fluorenyl, phenanthrenyl, phenyl, naphthyl, and the like.

The term "cycloalkyl" denotes a saturated monocyclic, or polycyclic, cycloalkyl group, optionally fused to an aryl group, wherein the cycloalkyl group optionally incorporates one or more double or triple bonds, or a combination of double bonds and triple bonds, but which is not aromatic. Examples of cycloalkyl groups include adamantanyl, cyclopropyl, cyclobutyl, cyclopentyl, cyclohexyl, cycloheptyl, decahydronaphthalinyl, norbornanyl, and the like.

The term "halogen" represents chloro, fluoro, bromo, and iodo.

The term "heteroaryl" denotes a monocyclic, or polycyclic, aromatic hydrocarbon group wherein one or more carbon atoms have been replaced with heteroatoms selected from the group consisting of nitrogen, oxygen, and sulfur. If the heteroaryl group contains more than one heteroatom, the heteroatoms may be the same or different. Examples of heteroaryl groups include acridinyl, benzofuranyl, benzothienyl, benzimidazolyl, benzoxazolyl, benzothiazolyl, chromenyl, cinnolinyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phenazinyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated, or partially unsaturated, monocyclic, or polycyclic, cycloalkyl group, optionally fused to an aromatic or heteroaromatic hydrocarbon group, in which at least one of the carbon atoms has been replaced with a heteroatom selected from the group consisting of nitrogen, oxygen, and sulfur. If the heterocycloalkyl group contains more than one heteroatom, the heteroatoms may be the same or different. Examples of such heterocycloalkyl groups include azabicycloheptanyl, azetidinyl, benzazepinyl, 1,3-dihydroisoindolyl, dioxolanyl, dioxanyl, carbazolyl, dioxolanyl, dithianyl, indolinyl, imidazolidinyl, morpholinyl, quinuclidinyl, phenothiazinyl, phenoxazinyl, piperazinyl, piperidyl, pyrazolidinyl, pyrrolidinyl, tetrahydrofuryl, tetrahydroindolyl, tetrahydroisoquinolinyl, tetrahydropyranyl, tetrahydroquinolinyl, tetrahydroquinoxalinyl, tetrahydrothiopyranyl, tetrahydro-2H-1,4-thiazinyl, thiazolidinyl, thiomorpholinyl, thioxanthenyl, thioxanyl, trithianyl, and the like.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "mammal" means animals including, for example, dogs, cats, cows, sheep, horses, and humans. Preferred mammals include humans of either gender.

The term "oxo", when used within the context of the term "heterocycloalkyl", indicates a carbonyl substituent formed between a ring carbon atom(s) of the heterocycloalkyl group and an oxygen atom.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the preparation and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e.g., an organic radical is a group of atoms that imparts characteristic properties to a compound containing it, or which remains unchanged during a series of reactions, or transformations.

The term "salts" refers to organic and inorganic salts of a compound of formula (I), or a prodrug thereof. These salts can be prepared in situ during the final isolation and purification of a compound, or by separately reacting a compound of formula (I), or a prodrug thereof, with a suitable organic or inorganic acid or base and isolating the salt thus formed. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds and prodrugs of formula (I) as well as mixtures thereof, including racemic mixtures, form part of the present invention. In addition, the present invention embraces all geometric and positional isomers. For example, if a compound or prodrug of formula (I) incorporates a double bond, both the cis- and trans-forms, as well as mixtures thereof, are embraced within the scope of the invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of formula (I) may be atropisomers (e.g., substituted biaryls) and are also considered as part of the invention.

The compounds and prodrugs of formula (I) may exist in unsolvated as well as solvated forms with pharmaceutically acceptable solvents, such as water, ethanol, and the like, and it is intended that the invention embrace both solvated and unsolvated forms.

It is also possible that the compounds and prodrugs of formula (I) may exist as tautomeric isomers in equilibrium, and all such forms are embraced within the scope of the invention.

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. The compounds of formula (I), the prodrugs thereof, and the pharmaceutically acceptable salts of the compounds and prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their relative ease of preparation and facile detection. Furthermore, substitution with heavier isotopes such as deuterium, i.e., $^2$H, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Schemes and/or Examples set forth hereinbelow, by substituting an isotopically-labeled reagent for a non-isotopically-labeled reagent.

In another aspect, the invention provides methods for inhibiting cdk2, cdk5, and/or GSK-3 activity in a mammal in need of such inhibition which methods comprise administering to the mammal a cdk2, cdk5, and/or GSK-3 activity inhibiting amount of a compound of formula (I), a prodrug thereof, or a pharmaceutically acceptable salt of the compound or prodrug; or a cdk2, cdk5, and/or GSK-3 activity inhibiting amount of a pharmaceutical composition comprising a compound of formula (I), a prodrug thereof, or a pharmaceutically acceptable salt of the compound or prodrug, and a pharmaceutically acceptable carrier, vehicle, or diluent.

In another aspect, the invention provides pharmaceutical compositions comprising an amount of a compound of formula (I), a prodrug thereof, or a pharmaceutically acceptable salt of the compound or prodrug, optionally in combination with an amount of one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), or a (xii) a potassium channel modulator.

In yet another aspect, the invention provides methods of treating cdk2, cdk5, and/or GSK-3 mediated conditions, diseases, or symptoms in a mammal in need of such treatment which methods comprise administering to the mammal: (i) a therapeutically effective amount of a compound of formula (I), a prodrug thereof, or a pharmaceutically acceptable salt of the compound or prodrug; (ii) a therapeutically effective amount of a pharmaceutical composition comprising a compound of formula (I), a prodrug thereof, or a pharmaceutically acceptable salt of the compound or prodrug, and a pharmaceutically acceptable carrier, vehicle, or diluent; (iii) a therapeutically effective amount of a combination of a compound of formula (I), a prodrug thereof, or a pharmaceutically acceptable salt of the compound or prodrug, and one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator; or (iv) a therapeutically effective amount of a pharmaceutical composition comprising the aforementioned combinations.

Preferred conditions, diseases, and symptoms treatable according to the methods of the instant invention are those selected from the group consisting of Alzheimer's Disease, asthma, atherosclerosis, anxiety, bipolar disorder, cancer, diabetes, dementia, depression, frailty, hair loss, heart failure, essential hypertension, hyperglycemia, hyperlipidemia, hypoglycemia, inflammation, ischemia, male fertility and sperm motility, mood disorders, neuronal cell death, obesity, obsessive compulsive disorder, polycystic ovary disorder, schizophrenia, stroke, Syndrome X, and traumatic brain injury.

Frailty is characterized by the progressive loss of skeletal muscle mass resulting in a high risk of injury from fall, difficulty in recovery from illness, prolongation of hospitalization, and long-term disability requiring assistance in daily living. The reduction of muscle mass and physical strength typically leads to diminished quality of life, loss of independence, and mortality. Frailty is normally associated with aging, but may also result when muscle loss and reduced strength occur due to other factors, such as disease-induced cachexia, immobilization, or drug-induced sarcopenia. Another term that has been used to denote frailty is sarcopenia, which is a generic term for the loss of skeletal muscle mass, or quality. Examples of skeletal muscle properties that contribute to its overall quality include contractility, fiber size and type, fatiguability, hormone responsiveness, glucose uptake/metabolism, and capillary density.

Generally preferred anti-angiogenesis agents may comprise, for example, matrix metalloproteinase-2 (MMP-2) inhibitors, matrix metalloproteinase-9 (MMP-9) inhibitors, and cyclooxygenase-II (COX-II) inhibitors. Examples of useful MMP-2 and MMP-9 inhibitors are disclosed in, for example, PCT International Application Publication Nos. WO 98/34915 and WO 98/34918, and U.S. Pat. Nos. 5,240,958; 5,310,763; 5,455,258; 5,506,242; 5,530,161; 5,552,419; 5,672,615; 5,861,510; 5,863,949; 5,932,595; 5,994,351; 6,077,864; 6,087,392; 6,090,852; 6,110,964; 6,147,061; 6,147,074; 6,303,636; 6,380,219; and 6,387,931. Examples of COX-II inhibitors useful in the present combinations and methods comprise CELEBREX® (celecoxib, U.S. Pat. No. 5,466,823), valdecoxib (U.S. Pat. No. 5,633,272), and rofecoxib (U.S. Pat. No. 5,474,995). Generally preferred MMP-2 and MMP-9 inhibitors are those exhibiting little or no activity inhibiting MMP-1. Especially preferred MMP-2 and MMP-9 inhibitors are those that selectively inhibit MMP-2 and/or MMP-9 relative to other MMP inhibitors, i.e., MMP-1, MMP-3, MMP-4, MMP-5, MMP-6, MMP-7, MMP-8, MMP-10, MMP-11, MMP-12, and MMP-13. Specific examples of MMP inhibitors useful in the present combinations and methods comprise AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonyl-amino]-8-oxa-bicyclo[3.2.1]octane-3-carboxylic acid hydroxyamide;

(2R,3R)1-[4-(2-chloro-fluoro-benzyloxy)-benzenesulfonyl]-3-hydroxy-3-methyl-piperidine-2-carboxylic acid hydroxyamide;

4-[4-(4-fluoro-phenoxy)-benzenesulfonyl-amino]-tetrahydro-pyran-4-carboxlyic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonyl-amino]-tetrahydro-pyran-4-carboxlyic acid hydroxyamide;

(R)-3-[4-(4-chloro-phenoxy)-benzenesulfonyl-amino]-tetrahydro-pyran-3-carboxlyic acid hydroxyamide;

(2R,3R)1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonyl-amino]-8-oxa-bicyclo[3.2.1]octane-3-carboxylic acid hydroxyamide;

3-endo-3-[4-(4-fluoro-phenoxy)-benzenesulfonyl-amino]-8-oxa-bicyclo[3.2.1]octane-3-carboxylic acid hydroxyamide; and (R)-3-[4-(4-fluoro-phenoxy)-benzenesulfonyl-amino]-tetrahydro-furan-3-carboxlyic acid hydroxyamide; and the pharmaceutically acceptable salts and solvates thereof.

Generally preferred signal transduction inhibitors may comprise, for example, epidermal growth factor receptor (EGFR) response inhibitors, such as EGFR antibodies, EGF antibodies, and molecules that are EGFR inhibitors; vascular endothelial growth factor (VEGF) inhibitors; and erbB2 receptor inhibitors, such as molecules or antibodies that bind to the erbB2 receptor, for example, HERCEPTIN® (Genentech Inc.; South San Francisco, Calif.). EGFR inhibitors are described in, for example, PCT International Application Publication No. WO 98/14451, and U.S. Pat. Nos. 5,679,683; 5,747,498; and 6,391,874. EGFR-inhibiting agents may comprise, for example, the monoclonal antibodies C225 and anti-EGFR 22Mab (Imclone Systems, Inc.), ZD-1839, BIBX-1382, Mbx-103, VRCTC-310, and EGF fusion toxin (Seragen Inc.; Hopkinton, Mass.). VEGF inhibitors are disclosed in, for example, PCT International Application Publication No. WO 99/24440, and U.S. Pat. Nos. 5,792,783; 5,834,504; 5,851,999; 5,883,113; 5,886,020; 6,051,593; 6,114,371; 6,133,305; 6,162,804; 6,174,889; 6,207,669; 6,235,741; 6,291,455; 6,294,532; 6,310,238; 6,380,203; and 6,395,734. Specific VEGF inhibitors may comprise, for example, Su-5416, IM862, anti-VEGF monoclonal antibody (Cytran Inc.; Kirkland, Wash.), and angiozyme (Ribozyme; Boulder, Colo.). ErbB2 receptor inhibitors are disclosed in, for example, PCT International Application Publication Nos. WO 97/13760, WO 99/35132, and WO, 99/35146, and U.S. Pat. Nos. 5,679,683; 5,587,458; 5,877,305; 6,207,669; and 6,391,874. Specific erbB2 receptor inhibitors may comprise, for example, GW-282974 (Glaxo Wellcome plc.), and the monoclonal antibody AR-209 (Aronex Pharmaceuticals Inc.; The Woodlands, Tex.).

Generally preferred anti-proliferative agents may comprise, for example, cytotoxic lymphocyte antigen 4 (CTLA4) antibodies, and other agents capable of blocking CTLA4; and farnesyl transferase inhibitors.

Examples of NK-1 receptor antagonists are disclosed in, for example, U.S. Pat. Nos. 5,122,525; 5,162,339; 5,232,929; 5,332,817; 5,703,240; 5,716,965; 5,719,147; 5,744,480; 5,763,699; 5,773,450; 5,807,867; 5,843,966; 5,852,038; 5,886,009; and 5,939,433.

Examples of 5HT$_{1D}$ receptor antagonists useful in the present combinations and methods are disclosed in, for example, PCT International Application Publication No. WO 94/21619, and U.S. Pat. Nos. 5,358,948; 5,510,350; 6,380,186; 6,403,592; 6,423,708; and 6,462,048.

Examples of SSRI's useful in the present combinations and methods may comprise, for example, fluoxetine (U.S. Pat. No. 4,314,081), paroxetine (U.S. Pat. No. 4,007,196), sertraline (U.S. Pat. No. 4,536,518), fluvoxamine (U.S. Pat. No. 4,085,225), venlafaxine hydrochloride (EFFEXOR®, U.S. Pat. No. 4,535,186), nefazodone hydrochloride (SERZONE®, U.S. Pat. No. 4,338,317), and bupropion hydrochloride (WELLBUTRIN®, U.S. Pat. Nos. 3,819,706 and 3,885,046).

Generally preferred anti-psychotic agents useful in the present combinations and methods may comprise, for example, ziprasidone (GEODON®, U.S. Pat. No. 5,312,925), olanzapine (U.S. Pat. No. 5,229,382), risperidone (U.S. Pat. No. 4,804,663), L-745,870, sonepiprazole, RP-62203 (fananserin), NGD-941, balaperidone, flesinoxan (U.S. Pat. No. 4,833,142), and gepirone (U.S. Pat. No. 4,423,049).

Generally preferred acetylcholinesterase inhibitors useful in the present combinations and methods may comprise, for example, donepezil (ARICEPT®, U.S. Pat. No. 4,895,841), rivastigmine (EXELON®, U.S. Pat. No. 4,948,807), metrifonate (U.S. Pat. No. 2,701,225), galanthamine, physostigmine, tacrine, huperzine, and icopezil (U.S. Pat. No. 5,538,984).

Generally preferred neuroprotectants useful in the instant combinations and methods may comprise, for example, NMDA receptor antagonists. Specific NMDA receptor antagonists comprise, for example, (1S,2S)-1-(4-hydroxyphenyl)-2-(4-hydroxy-4-phenylpiperidin-1-yl)-1-propanol (U.S. Pat. No. 5,272,160); eliprodil (U.S. Pat. No. 4,690,931); and gavestenel (U.S. Pat. No. 5,373,018). Examples of additional NMDA antagonists are disclosed in, for example, U.S. Pat. Nos. 4,690,931; 5,185,343; 5,272,160; 5,356,905; 5,373,018; 5,744,483; 5,962,472; 6,046,213; 6,124,317; 6,124,323; 6,130,234; 6,218,404; 6,333,036; and 6,448,270; and in PCT International Application Publication Nos. WO 97/23202 and WO 98/18793.

A generally preferred potassium channel modulator comprises, for example, BMS-204352 (flindokaliner, U.S. Pat. No. 5,602,169).

The disclosures of all of the above U.S. patents are incorporated herein in their entirety by reference.

The compounds of formula (I), the prodrugs thereof, and the pharmaceutically acceptable salts of the compounds and prodrugs, may be administered to a mammal at dosage levels in the range of from about 0.0001 mg to about 1,000 mg per day. For a normal adult human having a body mass of about 70 kg, a dosage in the range of from about 0.01 mg to about 500 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, the compounds of formula (I), the prodrugs thereof, and the pharmaceutically acceptable salts of the compounds and prodrugs, or the aforementioned combinations thereof, are preferably administered in the form of a pharmaceutical composition comprising a pharmaceutically acceptable carrier, vehicle, or diluent. Accordingly, an amount of a compound of formula (I), a prodrug thereof, or a pharmaceutically acceptable salt of the compound or prodrug, or the aforementioned combinations, may be administered to a subject separately, or together, in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of the aforementioned substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I), the prodrugs thereof, and the pharmaceutically acceptable salts of the compounds and prodrugs, may be prepared according to the exemplary synthetic routes disclosed in the Schemes and Examples hereinbelow, as well as by other conventional organic preparative methods known, or apparent in light of the instant disclosure, to one of ordinary skill in the relevant art. It is to be understood that the methods disclosed in the instant Schemes are intended for purposes of exemplifying the instant invention, and are not to be construed in any manner as limitations thereon.

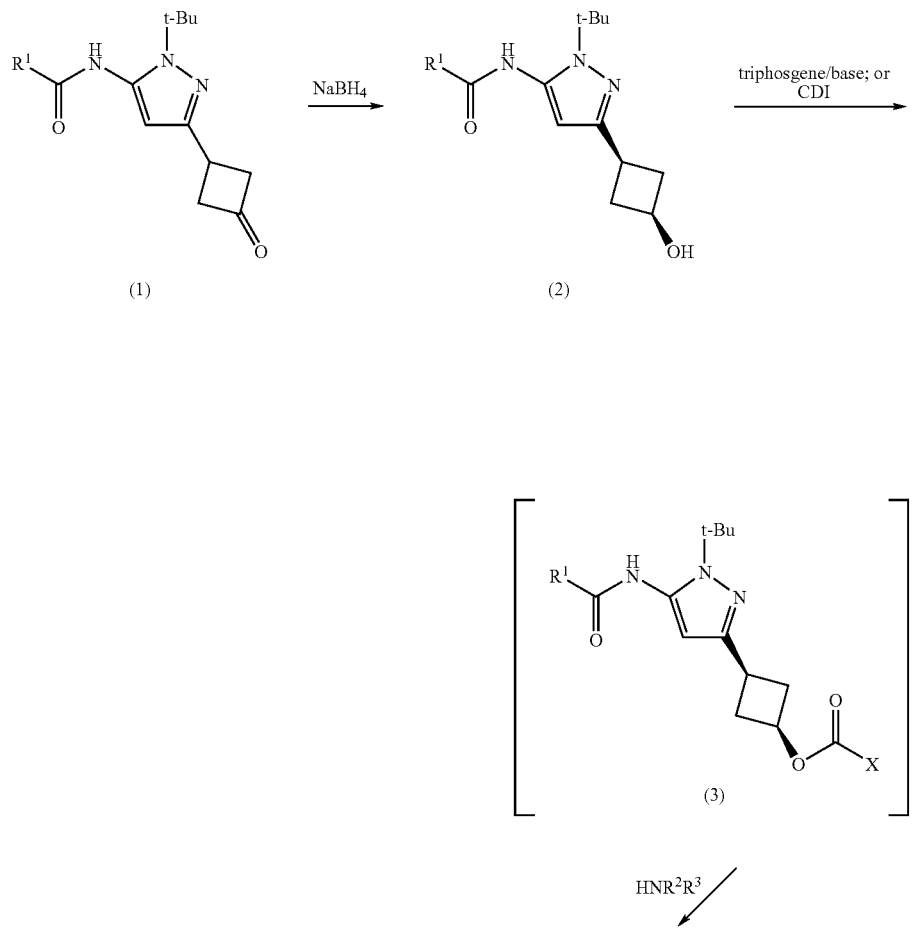

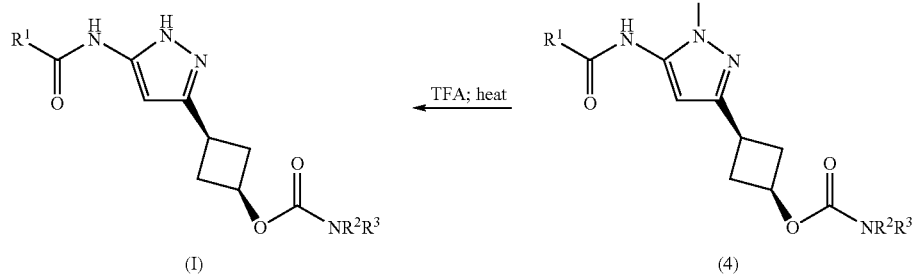

In Scheme 1, an appropriately-substituted cyclobutanone derivative (1), prepared as disclosed in the aforementioned PCT International Application Publication No. WO 02/18346, is treated with a reducing agent, preferably sodium borohydride, in a suitable solvent, such as a mixture of tetrahydrofuran (THF) and ethanol (EtOH), at below ambient temperature, preferably about −78° C., followed by warming to 0° C., or ambient temperature. It has been found that the cis isomer of the resulting cyclobutanol (2) is formed predominantly over the corresponding trans isomer, typically in ratios of >10:1. Cyclobutanol (2) is treated with a carbonic acid equivalent, preferably triphosgene or 1,1'-carbonyldiimidazole (CDI), to form the activated intermediate (3), in a solvent such as ethyl acetate (EtOAc) or methylene chloride, at or below ambient temperature. An amine base, preferably pyridine, is added to reactions utilizing triphosgene, and may optionally be employed for reactions using CDI. Addition of an appropriately-substituted amine $HNR^2R^3$ to the solution of (3), typically at a temperature of between ambient temperature and the reflux temperature of the solvent employed, affords protected pyrazole (4). The tert-butyl protecting group is cleaved by treating (4) with trifluoroacetic acid (TFA), at elevated temperature, preferably >70° C., to afford (I).

Alternatively, the compounds of formula (I) may be prepared according to the method disclosed in Scheme 2.

Scheme 2

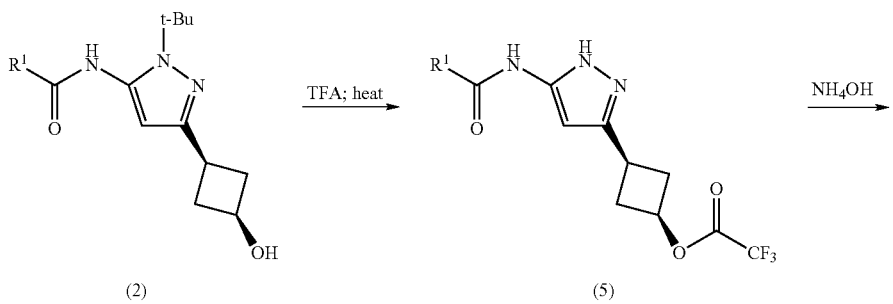

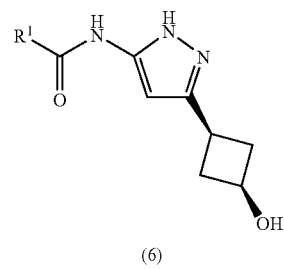

-continued

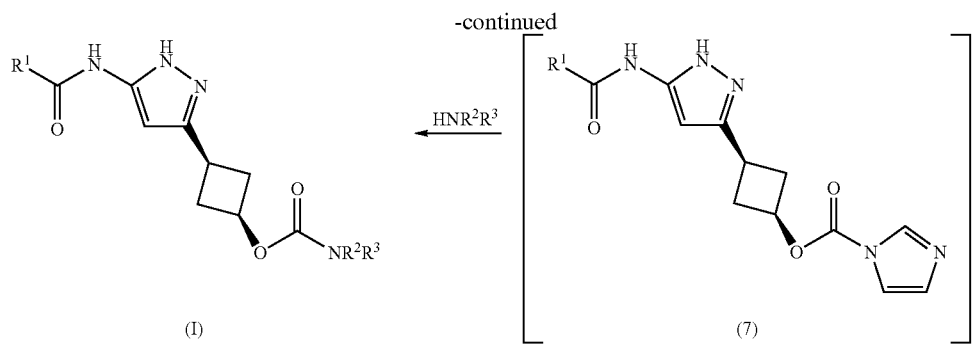

In Scheme 2, the tert-butyl protecting group of compound (2) is cleaved by treatment with an acid, preferably TFA, at elevated temperature. The resulting ester (5) is cleaved by treatment with an aqueous base, such as ammonium hydroxide or sodium hydroxide, to provide alcohol (6). Alcohol (6) is then treated with CDI in an organic solvent, preferably EtOAc, to afford intermediate imidazolide (7) which, if desired, may be isolated by conventional workup. The reaction of an appropriately-substituted amine $HNR^2R^3$ with (7) is effected in an organic solvent, preferably EtOAc, provides (I). Where needed, an amine base, such as triethylamine ($Et_3N$), 4-(dimethylamino)pyridine (DMAP), or a polymer-supported DMAP derivative, may be added. When an elevated temperature is required, such temperatures may be achieved by known methods, including heating the reaction in a microwave apparatus.

Alternatively, the compounds of formula (I) may be prepared according to the method disclosed in Scheme 3.

In Scheme 3, the tert-butyl protecting group of compound (1) is removed by treatment with acid as described hereinabove in Scheme 2. Deprotected pyrazole (8) is then treated with di-tert-butyldicarbonate in the presence of a base, preferably $Et_3N$ and DMAP, in an aprotic solvent such as methylene chloride, at ambient temperature. The resulting Boc-protected pyrazole (9) is isolated as a mixture of carbamate isomers that may be employed subsequently without further purification. Pyrazole (9) is treated with a reducing agent, preferably sodium borohydride, in a suitable solvent, such as a mixture of THF and EtOH, at or below ambient temperature, to afford alcohol (10). Reaction of (10) with an appropriately-substituted amine $HNR^2R^3$ affords (11) which is then deprotected by treatment with an acid, such as TFA or, alternatively, by warming a solution of (11) in acetonitrile or dimethylsulfoxide (DMSO) in a microwave apparatus at about 150° C.

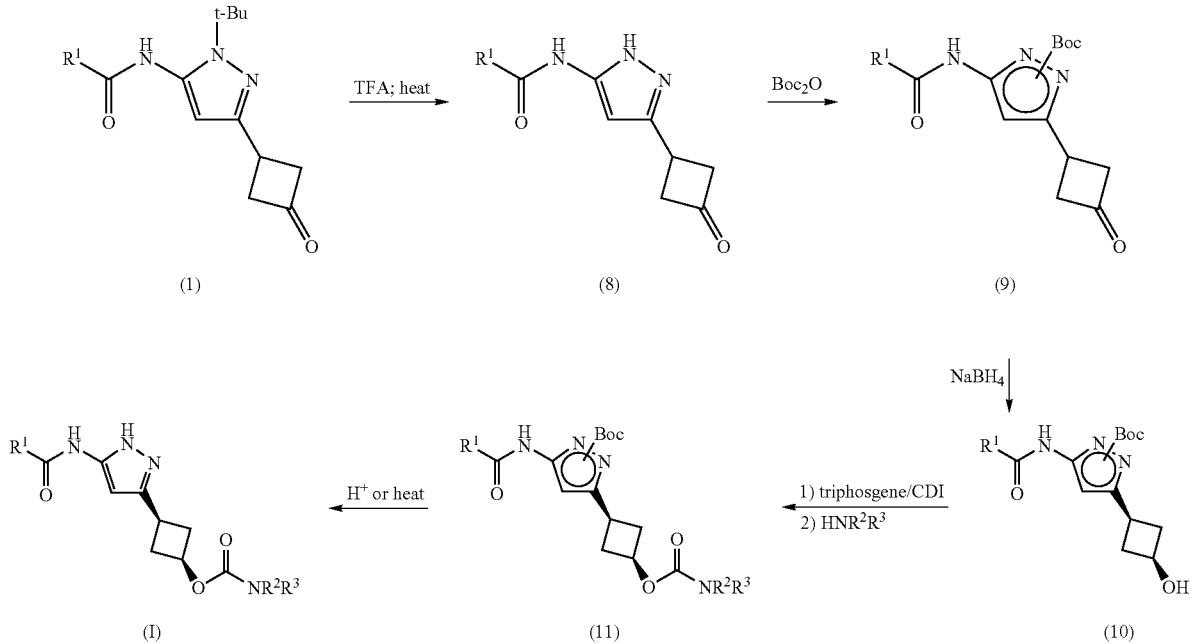

Alternatively, the compounds of formula (I) may be according prepared according to the method disclosed in Scheme 4.

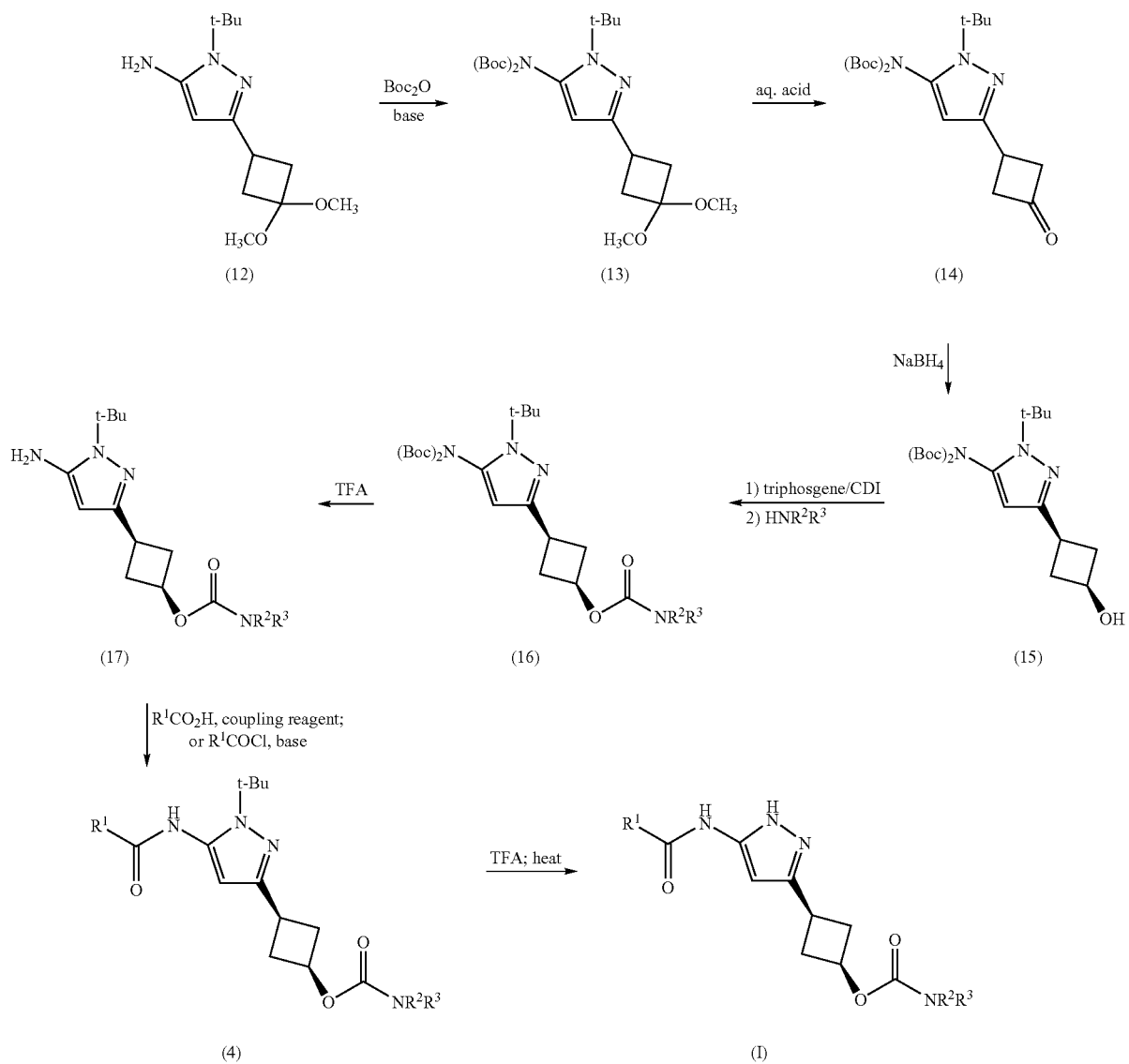

Scheme 4

In Scheme 4, compound (12), prepared as disclosed in the aforementioned PCT International Application Publication No. WO 02/18346, is treated with an excess of di-tert-butyl-dicarbonate in the presence of a base, preferably $Et_3N$ and DMAP, in an aprotic solvent such as methylene chloride, at ambient temperature, to provide the bis-carbamoylated product (13). Treatment of (13) with aqueous acid, preferably p-toluenesulfonic acid, in a mixture of water and acetone, preferably at reflux temperature, affords ketone (14). Ketone (14) is then treated with a reducing agent, preferably sodium borohydride, in a suitable solvent, such as a mixture of THF and EtOH, at below ambient temperature, preferably –78° C., followed by warming to 0° C., or ambient temperature. As in Scheme 1, it has been found that the cis isomer of the resulting cyclobutanol (15) is formed predominantly over the corresponding trans isomer, typically in ratios of ~10:1. Cyclobutanol (15) is then treated with a carbonic acid equivalent, preferably triphosgene or CDI, in a solvent such as EtOAc or methylene chloride, at or below ambient temperature. An amine base, preferably pyridine, is added to reactions untilizing triphosgene, and may optionally be employed for reactions using CDI. Addition of an appropriately-substituted amine $HNR^2R^3$, typically at a temperature of between ambient temperature and the reflux temperature of the solvent employed, affords protected pyrazole (16). The tert-butyl carbamate protecting groups are cleaved by treating (16) with trifluoroacetic acid (TFA) at ambient temperature to afford amine (17). Amine (17) is then treated under standard acylation conditions, with either a carboxylic acid and an amine coupling reagent, or a carboxylic acid chloride, and a base, such as $Et_3N$ or pyridine, to afford (4). The tert-butyl protecting group is cleaved by treating (4) with trifluoroacetic acid (TFA), at elevated temperature, preferably >70° C., to furnish compound (I).

PREPARATIVE EXPERIMENTAL

Unless otherwise noted, all reagents employed were obtained commercially. Unless otherwise noted, the following experimental abbreviations have the meanings indicated:

DMF—dimethylformamide
$Et_3SiH$—triethylsilane
HPLC—high performance liquid chromatography
h—hour(s)
M—molar
MeOH—methanol
min—minute(s)
IPA—isopropanol
mL—milliliter(s)
mmol—millimole(s)
HPLC—high performance liquid chromatography
MS—mass spectrometry Unless otherwise noted, preparation of the various N-(5-cyclobutyl-1H-pyrazol-3-yl)-amide starting materials from 2-tert-butyl-5-(3,3-dimethoxy-cyclobutyl)-2H-pyrazol-3-ylamine was carried out according to the methods described in the aforementioned PCT International Application Publication No. WO02/18346. 2-Methyl-tetrahydro-furan-2-carboxylic acid and 4-methyl-tetrahydro-pyran-4-carboxylic acid were prepared from tetrahydro-furan-2-carboxylic acid methyl ester and tetrahydro-pyran-4-carboxylic acid methyl ester, respectively, according to the method of Regan (J. Med. Chem., 45, 2994-3008 (2002)). Carboxylic acid chlorides that were not commercially available were prepared from the corresponding carboxylic acids by treatment with thionyl chloride (Org. Syn., Coll. Vol., 3, 169 (1955)).

Preparative reversed-phase HPLC purifications were carried out on a system obtained from Shimadzu Scientific Instruments, Inc.; Columbia, Md. (Model LC-8A Prep LC, SPD-10A UV-vis detector, FRC-10A fraction collector, SIL-10AP auto-injector). All microwave chemistry was performed using an Emrys Optimizer® (Personal Chemistry Inc.; Foxboro, Mass.).

Preparation 1

2-Methyl-2-pyridin-2-yl-propionic acid ethyl ester and 2-Pyridin-2-yl-propionic acid ethyl ester A solution of n-butyllithium in hexanes (2.5 M, 121 mL) was added slowly to a solution of diisopropylamine (42 mL) in THF (120 mL) at −78° C., and the resulting solution was stirred for 15 min. Pyridin-2-yl-acetic acid ethyl ester (9.2 mL) was then added and the mixture was stirred for 30 min before iodomethane (18.9 mL) was added. The reaction mixture was stirred at −78° C. for 15 min and then at room temperature for 3 h. The reaction mixture was diluted with water and extracted with $CH_2Cl_2$ (3×). After concentration, the residue was purified by silica gel chromatography to afford the title compounds separately. 2-Methyl-2-pyridin-2-yl-propionic acid ethyl ester: MS $(M+H)^+$=194.1. 2-Pyridin-2-yl-propionic acid ethyl ester: MS $(M+H)^+$=180.1.

EXAMPLE 1

Benzyl-carbamic acid cis-3-[5-(2-methyl-2-pyridin-2-yl-propionylamino)-2H-pyrazol-3-yl]-cyclobutyl ester Step A A solution of trimethylaluminum in heptane (2.0 M, 19.5 mL) was added slowly to a solution of 2-tert-butyl-5-(3,3-dimethoxy-cyclobutyl)-2H-pyrazol-3-ylamine (8.98 g) in $CH_2Cl_2$ (60 mL) at room temperature. After 15 min, a solution of 2-methyl-2-pyridin-2-yl-propionic acid ethyl ester (6.85 g) in $CH_2Cl_2$ (60 mL) was added. The reaction mixture was heated to reflux overnight. Saturated aqueous $NH_4Cl$ solution was added and the mixture was extracted with $CH_2Cl_2$ (2×). The combined organic layers were dried over $Na_2SO_4$ and concentrated to afford N-[2-tert-butyl-5-(3,3-dimethoxy-cyclobutyl)-2H-pyrazol-3-yl]-2-pyridin-2-yl-isobutyramide as an oil that was used without further purification.

Step B

A mixture of the product of Step A (1.0 g) and p-toluenesulfonic acid monohydrate (50 mg) in water (0.7 mL) and acetone (9 mL) was heated at reflux for 7 h. The solution was cooled, concentrated, and the resulting residue was partitioned between EtOAc and saturated aqueous $NaHCO_3$ solution. The organic layer was dried over $Na_2SO_4$ and concentrated to afford the product ketone that was used without further purification.

Step C

Sodium borohydride (118 mg) was added to a solution of the product of Step B (1 g) in THF (9 mL) and EtOH (1.3 mL) at −78° C. The reaction mixture was stirred for 15 min at −78° C. and then at 0° C., and saturated aqueous $NH_4Cl$ solution was added to quench excess hydride. The mixture was extracted with $CH_2Cl_2$ (3×) and the combined organic layers were dried over $Na_2SO_4$ and concentrated. The alcohol product was purified by silica gel chromatography.

Step D

To a solution of the product of Step C (50 mg) in $CH_2Cl_2$ (0.5 mL) at 0° C. was added sequentially a solution of triphosgene (29 mg) in $CH_2Cl_2$ (0.5 mL) and pyridine (0.036 mL). The mixture was stirred at room temperature for 1 h, and benzylamine (45 mg) was added. After 3 h, saturated aqueous $NH_4Cl$ solution was added and the mixture was extracted with $CH_2Cl_2$ (3×). The combined organic layers were dried over $Na_2SO_4$ and concentrated. The residue was purified by silica gel chromatography to afford the product carbamate.

Step E

A solution of the product of Step E (48 mg), $Et_3SiH$ (0.046 mL), and TFA (1 mL) was heated to reflux for 12 h. The solution was concentrated and the residue partitioned between saturated aqueous $NaHCO_3$ solution and $CH_2Cl_2$. The organic layer was dried over $Na_2SO_4$ and concentrated. The residue was purified by silica gel chromatography to afford the title product as a white solid. MS $(M+H)^+$=434.2.

The following compounds were prepared in a manner analogous to that described in Example 1 using appropriate starting materials.

| Example | Name | MS (M + H)+ |
|---|---|---|
| 2 | Benzyl-methyl-carbamic acid cis-3-[5-(2-methyl-2-pyridin-2-yl-propionylamino)-2H-pyrazol-3-yl]-cyclobutyl ester | 448.2 |
| 3 | Isobutyl-carbamic acid cis-3-[5-(2-methyl-2-pyridin-2-yl-propionylamino)-2H-pyrazol-3-yl]-cyclobutyl ester | 400.2 |

The following compounds were prepared in a manner analogous to that ample 1, Steps C to E, using appropriate starting materials.

| Example | Name | MS (M + H)+ |
|---|---|---|
| 4 | Benzyl-ethyl-carbamic acid cis-3-{5-[((R)-tetrahydro-furan-2-carbonyl)-amino]-1H-pyrazol-3-yl}-cyclobutyl ester | 413.4 |
| 5 | Methyl-pyridin-3-ylmethyl-carbamic acid cis-3-(5-isobutyrylamino-1H-pyrazol-3-yl)-cyclobutyl ester | 372.4 |
| 6 | 1,3-Dihydro-isoindole-2-carboxylic acid cis-3-(5-isobutyrylamino-1H-pyrazol-3-yl)-cyclobutyl ester | 369.4 |
| 7 | Methyl-phenyl-carbamic acid cis-3-(5-isobutyrylamino-1H-pyrazol-3-yl)-cyclobutyl ester | 357.4 |
| 8 | Phenyl-carbamic acid cis-3-(5-isobutyrylamino-1H-pyrazol-3-yl)-cyclobutyl ester | 343.4 |

EXAMPLE 9

Cyclohexylmethyl-carbamic acid cis-3-[5-(3-pyrazol-1-yl-propionylamino)-1H-pyrazol-3-yl]-cyclobutyl ester Step A A solution of N-[2-tert-butyl-5-(cis-3-hydroxy-cyclobutyl)-2H-pyrazol-3-yl]-3-pyrazol-1-yl-propionamide (200 mg, prepared as in Example 1, Step C using appropriate starting materials) and CDI (100 mg) in EtOAc (3 mL) was stirred at room temperature. After 45 min, cyclohexyl-methylamine (0.12 mL) was added and the solution was heated at reflux overnight. The solution was cooled and then diluted with EtOAc and washed sequentially with portions of saturated aqueous NH$_4$Cl solution, saturated aqueous NaHCO$_3$ solution, and saturated aqueous NaCl solution. The organic layer was dried over Na$_2$SO$_4$ and then concentrated. The residue was purified by silica gel chromatography to afford the product carbamate as a white solid.

Step B

A solution of cyclohexylmethyl-carbamic acid cis-3-[1-tert-butyl-5-(3-pyrazol-1-yl-propionylamino)-1H-pyrazol-3-yl]-cyclobutyl ester from Step A (122 mg) in TFA (2 mL) was heated at 120° C. in a microwave apparatus for 10 min. The solution was concentrated and the residue was dissolved in EtOAc. The resulting solution was washed sequentially with portions of saturated aqueous NaHCO$_3$ solution and saturated aqueous NaCl solution. The organic layer was dried over Na$_2$SO$_4$ and concentrated. The residue was purified by silica gel chromatography to afford the title product as a white solid. MS (M+H)+=415.5.

The following compounds were prepared in a manner analogous to that described in Example 9 using appropriate starting materials. For Examples designated with an asterisk, Step B was conducted in TFA at reflux overnight.

| Example | Name | MS (M + H)+ |
|---|---|---|
| 10 | Diethyl-carbamic acid cis-3-[5-(cyclohexanecarbonyl-amino)-1H-pyrazol-3-yl]-cyclobutyl ester | 363.4 |
| 11 | (2-Methoxy-1-methyl-ethyl)-carbamic acid cis-3-[5-(cyclohexanecarbonyl-amino)-1H-pyrazol-3-yl]-cyclobutyl ester | 379.4 |
| 12 | (2-Methoxy-ethyl)-carbamic acid cis-3-[5-(cyclohexanecarbonyl-amino)-1H-pyrazol-3-yl]-cyclobutyl ester | 365.4 |
| 13 | (2-Dimethylamino-ethyl)-methyl-carbamic acid cis-3-[5-(cyclohexanecarbonyl-amino)-1H-pyrazol-3-yl]-cyclobutyl ester | 392.4 |
| 14 | Isobutyl-carbamic acid cis-3-[5-(cyclohexanecarbonyl-amino)-1H-pyrazol-3-yl]-cyclobutyl ester | 363.4 |
| 15 | Benzyl-methyl-carbamic acid cis-3-{5-[(tetrahydro-pyran-4-carbonyl)-amino]-1H-pyrazol-3-yl}-cyclobutyl ester | 413.4 |
| 16 | (2-Methoxy-ethyl)-methyl-carbamic acid cis-3-{5-[(tetrahydro-pyran-4-carbonyl)-amino]-1H-pyrazol-3-yl}-cyclobutyl ester | 381.4 |
| 17* | Benzyl-carbamic acid cis-3-{5-[(tetrahydro-pyran-4-carbonyl)-amino]-1H-pyrazol-3-yl}-cyclobutyl ester | 399.4 |
| 18* | Piperidine-1-carboxylic acid cis-3-{5-[(tetrahydro-pyran-4-carbonyl)-amino]-1H-pyrazol-3-yl}-cyclobutyl ester | 377.4 |
| 19 | Isopropyl-methyl-carbamic acid cis-3-[5-(cyclohexanecarbonyl-amino)-1H-pyrazol-3-yl]-cyclobutyl ester | 363.4 |
| 20 | (2-Pyridin-3-yl-ethyl)-carbamic acid cis-3-[5-(cyclohexanecarbonyl-amino)-1H-pyrazol-3-yl]-cyclobutyl ester | 412.3 |
| 21* | (2-Chloro-benzyl)-carbamic acid cis-3-{5-[(tetrahydro-pyran-4-carbonyl)-amino]-1H-pyrazol-3-yl}-cyclobutyl ester | 433.3 |
| 22* | Pyridin-2-ylmethyl-carbamic acid cis-3-{5-[(tetrahydro-pyran-4-carbonyl)-amino]-1H-pyrazol-3-yl}-cyclobutyl ester | 400.4 |
| 23* | (3-Chloro-benzyl)-carbamic acid cis-3-{5-[(tetrahydro-pyran-4-carbonyl)-amino]-1H-pyrazol-3-yl}-cyclobutyl ester | 433.3 |
| 24 | Phenethyl-carbamic acid cis-3-{5-[(tetrahydro-pyran-4-carbonyl)-amino]-1H-pyrazol-3-yl}-cyclobutyl ester | 413.4 |
| 25 | Pyridin-3-ylmethyl-carbamic acid cis-3-{5-[(tetrahydro-pyran-4-carbonyl)-amino]-1H-pyrazol-3-yl}-cyclobutyl ester | 400.4 |
| 26 | 3,4-Dihydro-1H-isoquinoline-2-carboxylic acid cis-3-{5-[(tetrahydro-pyran-4-carbonyl)-amino]-1H-pyrazol-3-yl}-cyclobutyl ester | 425.6 |
| 27 | Benzyl-methyl-carbamic acid cis-3-[5-(3-pyrazol-1-yl-propionylamino)-1H-pyrazol-3-yl]-cyclobutyl ester | 423.5 |

-continued

| Example | Name | MS (M + H)+ |
|---|---|---|
| 28 | Benzyl-carbamic acid cis-3-[5-(3-pyrazol-1-yl-propionylamino)-1H-pyrazol-3-yl]-cyclobutyl ester | 409.4 |
| 29 | Methyl-propyl-carbamic acid cis-3-[5-(3-pyrazol-1-yl-propionylamino)-1H-pyrazol-3-yl]-cyclobutyl ester | 375.4 |
| 30* | Pyridin-2-ylmethyl-carbamic acid cis-3-[5-(3-pyrazol-1-yl-propionylamino)-1H-pyrazol-3-yl]-cyclobutyl ester | 410.4 |
| 31 | Propyl-carbamic acid cis-3-[5-(3-pyrazol-1-yl-propionylamino)-1H-pyrazol-3-yl]-cyclobutyl ester | 361.4 |
| 32 | Benzyl-carbamic acid cis-3-{5-[((R)-tetrahydro-furan-2-carbonyl)-amino]-1H-pyrazol-3-yl}-cyclobutyl ester | 385.4 |
| 33 | Pyridin-2-ylmethyl-carbamic acid cis-3-{5-[((R)-tetrahydro-furan-2-carbonyl)-amino]-1H-pyrazol-3-yl}-cyclobutyl ester | 386.4 |
| 34 | Isobutyl-carbamic acid cis-3-{5-[((R)-tetrahydro-furan-2-carbonyl)-amino]-1H-pyrazol-3-yl}-cyclobutyl ester | 351.4 |
| 35 | Benzyl-methyl-carbamic acid cis-3-{5-[((R)-tetrahydro-furan-2-carbonyl)-amino]-1H-pyrazol-3-yl}-cyclobutyl ester | 399.4 |
| 36* | [2-(3,5-Dimethyl-pyrazol-1-yl)-ethyl]-carbamic acid cis-3-[5-(3-pyrazol-1-yl-propionylamino)-1H-pyrazol-3-yl]-cyclobutyl ester | 441.4 |
| 37* | Benzyl-carbamic acid cis-3-(5-isobutyrylamino-1H-pyrazol-3-yl)-cyclobutyl ester | 357.4 |
| 38 | (Tetrahydro-furan-2-ylmethyl)-carbamic acid cis-3-(5-isobutyrylamino-1H-pyrazol-3-yl)-cyclobutyl ester | 351.4 |
| 39 | (2-Phenoxy-ethyl)-carbamic acid cis-3-[5-(3-pyrazol-1-yl-propionylamino)-1H-pyrazol-3-yl]-cyclobutyl ester | 439.4 |
| 40 | 3,4-Dihydro-1H-isoquinoline-2-carboxylic acid cis-3-[5-(3-pyrazol-1-yl-propionylamino)-1H-pyrazol-3-yl]-cyclobutyl ester | 435.4 |
| 41* | Dimethyl-carbamic acid cis-3-[5-(2-methyl-2-pyridin-2-yl-propionylamino)-2H-pyrazol-3-yl]-cyclobutyl ester | 372.3 |

EXAMPLE 42

Ethyl-carbamic acid cis-3-[5-(2-methyl-2-phenyl-propionylamino)-2H-pyrazol-3-yl]-cyclobutyl ester Step A Sodium borohydride (330 mg) was added to a solution of N-[2-tert-butyl-5-(3-oxo-cyclobutyl)-2H-pyrazol-3-yl]-2-phenyl-isobutyramide (2.8 g) in THF (100 mL) and EtOH (10 mL) at −60° C. The mixture was warmed to room temperature, and held at that temperature for 1.5 h. Excess hydride was quenched by the addition of MeOH (50 mL). The mixture was concentrated and the resulting residue was dissolved in EtOAc. The solution was washed sequentially with saturated aqueous K₂CO₃ solution (2×) and saturated aqueous NaCl solution. The organic layer was dried over Na₂SO₄ and concentrated to afford the product alcohol as a light yellow solid that was used without further purification.

Step B

A solution of the product of Step A (2.8 g) in TFA (50 mL) was heated to reflux for 48 h. The solution was concentrated and the resulting residue was dissolved in EtOAc. The solution was washed sequentially with saturated aqueous NaHCO₃ solution and saturated aqueous NaCl solution. The organic layer was dried over Na₂SO₄ and concentrated to afford the product ester as a residue that was used without further purification.

Step C

A solution of the product of Step B (1.9 g), concentrated aqueous NH₄OH (10 mL), and MeOH (20 mL) was heated to 65° C. for 90 min. The solution was concentrated, the resulting residue was diluted with EtOAc, and the solution washed sequentially with portions of saturated aqueous NaHCO₃ solution and saturated aqueous NaCl solution. The organic layer was dried over Na₂SO₄ and concentrated to afford the product alcohol as a solid that was used without further purification.

Step D

A mixture of the product of Step C (1.1 g) and CDI (714 mg) in EtOAc (30 mL) was stirred for 3 h. The solution was diluted with EtOAc and washed sequentially with portions of saturated aqueous NaHCO₃ solution and saturated aqueous NaCl solution. The organic layer was dried over Na₂SO₄ and concentrated to afford the product imidazolide as a solid that was used without further purification.

Step E

A mixture of the product of Step D (100 mg), PS-DMAP resin (0.15 mmol; Argonaut Technologies; Foster City, Calif.), and ethylamine hydrochloride (27 mg) in EtOAc (2 mL) was heated at 35° C. for 10 h. The resin was removed by filtration and the filtrate was concentrated. The resulting residue was purified by reversed-phase preparative HPLC to afford the title product as a white solid. MS (M+H)+=371.2.

The following compounds were prepared in a manner analogous to that described in Example 42 using appropriate starting materials. For Examples 43 to 71, DMAP was used in Step E, rather than PS-DMAP resin.

| Example | Name | MS (M + H)+ or MS (M − H)− |
|---|---|---|
| 43 | (2-Cyano-ethyl)-methyl-carbamic acid cis-3-[5-(cyclohexanecarbonyl-amino)-1H-pyrazol-3-yl]-cyclobutyl ester | 374.4 (+) |
| 44 | (3-Chloro-benzyl)-carbamic acid cis-3-[5-(cyclohexanecarbonyl-amino)-1H-pyrazol-3-yl]-cyclobutyl ester | 431.4 (+) |
| 45 | (2-Chloro-benzyl)-carbamic acid cis-3-{5-[((R)-tetrahydro-furan-2-carbonyl)-amino]-1H-pyrazol-3-yl}-cyclobutyl ester | 419.4 (+) |
| 46 | (3-Chloro-benzyl)-carbamic acid cis-3-{5-[((R)-tetrahydro-furan-2-carbonyl)-amino]-1H-pyrazol-3-yl}-cyclobutyl ester | 419.4 (+) |
| 47 | (4-Chloro-benzyl)-carbamic acid cis-3-{5-[((R)-tetrahydro-furan-2-carbonyl)-amino]-1H-pyrazol-3-yl}-cyclobutyl ester | 419.4 (+) |
| 48 | (4-Methoxy-benzyl)-carbamic acid cis-3-{5-[((R)-tetrahydro-furan-2-carbonyl)-amino]-1H-pyrazol-3-yl}-cyclobutyl ester | 415.4 (+) |
| 49 | (2,2-Dimethyl-propyl)-carbamic acid cis-3-{5-[((R)-tetrahydro-furan-2-carbonyl)-amino]-1H-pyrazol-3-yl}-cyclobutyl ester | 365.5 (+) |

-continued

| Example | Name | MS (M + H)+ or MS (M − H)− |
|---|---|---|
| 50 | (2-Phenylamino-ethyl)-carbamic acid cis-3-{5-[((R)-tetrahydro-furan-2-carbonyl)-amino]-1H-pyrazol-3-yl}-cyclobutyl ester | 414.4 (+) |
| 51 | Cyclohexylmethyl-carbamic acid cis-3-{5-[((R)-tetrahydro-furan-2-carbonyl)-amino]-1H-pyrazol-3-yl}-cyclobutyl ester | 391.5 (+) |
| 52 | (2-Isopropoxy-ethyl)-carbamic acid cis-3-{5-[((R)-tetrahydro-furan-2-carbonyl)-amino]-1H-pyrazol-3-yl}-cyclobutyl ester | 381.4 (+) |
| 53 | 3,4-Dihydro-1H-isoquinoline-2-carboxylic acid cis-3-{5-[((R)-tetrahydro-furan-2-carbonyl)-amino]-1H-pyrazol-3-yl}-cyclobutyl ester | 411.3 (+) |
| 54 | (4-Isopropyl-benzyl)-carbamic acid cis-3-{5-[((R)-tetrahydro-furan-2-carbonyl)-amino]-1H-pyrazol-3-yl}-cyclobutyl ester | 427.4 (+) |
| 55 | (2-Fluoro-benzyl)-carbamic acid cis-3-{5-[((R)-tetrahydro-furan-2-carbonyl)-amino]-1H-pyrazol-3-yl}-cyclobutyl ester | 403.3 (+) |
| 56 | Cyclopropylmethyl-carbamic acid cis-3-{5-[((R)-tetrahydro-furan-2-carbonyl)-amino]-1H-pyrazol-3-yl}-cyclobutyl ester | 349.3 (+) |
| 57 | (2-Phenyl-propyl)-carbamic acid cis-3-{5-[((R)-tetrahydro-furan-2-carbonyl)-amino]-1H-pyrazol-3-yl}-cyclobutyl ester | 413.4 (+) |
| 58 | (4-Cyano-cyclohexylmethyl)-carbamic acid cis-3-{5-[((R)-tetrahydro-furan-2-carbonyl)-amino]-1H-pyrazol-3-yl}-cyclobutyl ester | 416.4 (+) |
| 59 | (2-Piperidin-1-yl-ethyl)-carbamic acid cis-3-{5-[((R)-tetrahydro-furan-2-carbonyl)-amino]-2H-pyrazol-3-yl}-cyclobutyl ester | 406.3 (+) |
| 60 | (2-Chloro-6-fluoro-benzyl)-carbamic acid cis-3-{5-[((R)-tetrahydro-furan-2-carbonyl)-amino]-2H-pyrazol-3-yl}-cyclobutyl ester | 437.2 (+) |
| 61 | (2,4-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 62 | (2,3-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 63 | (2-Methyl-benzyl)-carbamic acid cis-3-{5-[((R)-tetrahydro-furan-2-carbonyl)-amino]-2H-pyrazol-3-yl}-cyclobutyl ester | 399.2 (+) |
| 64 | (2,6-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 65 | (2-Fluoro-3-trifluoromethyl-benzyl)-carbamic acid cis-3-{5-[((R)-tetrahydro-furan-2-carbonyl)-amino]-2H-pyrazol-3-yl}-cyclobutyl ester | 471.2 (+) |
| 66 | tert-Butyl-carbamic acid cis-3-{5-[((R)-tetrahydro-furan-2-carbonyl)-amino]-1H-pyrazol-3-yl}-cyclobutyl ester | 351.3 (+) |
| 67 | (2-Phenoxy-ethyl)-carbamic acid cis-3-{5-[((R)-tetrahydro-furan-2-carbonyl)-amino]-1H-pyrazol-3-yl}-cyclobutyl ester | 415.2 (+) |
| 68 | (2-Methoxy-benzyl)-carbamic acid cis-3-{5-[((R)-tetrahydro-furan-2-carbonyl)-amino]-1H-pyrazol-3-yl}-cyclobutyl ester | 415.2 (+) |

-continued

| Example | Name | MS (M + H)+ or MS (M − H)− |
|---|---|---|
| 69 | (2-Trifluoromethyl-benzyl)-carbamic acid cis-3-{5-[((R)-tetrahydro-furan-2-carbonyl)-amino]-1H-pyrazol-3-yl}-cyclobutyl ester | 453.2 (+) |
| 70 | (2-Fluoro-5-trifluoromethyl-benzyl)-carbamic acid cis-3-{5-[((R)-tetrahydro-furan-2-carbonyl)-amino]-1H-pyrazol-3-yl}-cyclobutyl ester | 471.2 (+) |
| 71 | (2,5-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 72 | (1H-Benzoimidazol-2-ylmethyl)-carbamic acid cis-3-{5-[((R)-tetrahydro-furan-2-carbonyl)-amino]-2H-pyrazol-3-yl}-cyclobutyl ester | 423.1 (−) |
| 73 | (2-Pyridin-2-yl-ethyl)-carbamic acid cis-3-{5-[((R)-tetrahydro-furan-2-carbonyl)-amino]-2H-pyrazol-3-yl}-cyclobutyl ester | 398.2 (−) |
| 74 | (2-Pyrrolidin-1-yl-ethyl)-carbamic acid cis-3-{5-[((R)-tetrahydro-furan-2-carbonyl)-amino]-1H-pyrazol-3-yl}-cyclobutyl ester | 392.4 (+) |
| 75 | (1-Ethyl-pyrrolidin-2-ylmethyl)-carbamic acid cis-3-{5-[((R)-tetrahydro-furan-2-carbonyl)-amino]-2H-pyrazol-3-yl}-cyclobutyl ester | 406.4 (+) |
| 76 | (2-Morpholin-4-yl-ethyl)-carbamic acid cis-3-{5-[((R)-tetrahydro-furan-2-carbonyl)-amino]-2H-pyrazol-3-yl}-cyclobutyl ester | 408.3 (+) |
| 77 | [2-(cis-3-{5-[((R)-Tetrahydro-furan-2-carbonyl)-amino]-2H-pyrazol-3-yl}-cyclobutoxycarbonylamino)-ethyl]-carbamic acid tert-butyl ester | 438.4 (+) |
| 78 | (2-Dimethylamino-ethyl)-carbamic acid cis-3-{5-[((R)-tetrahydro-furan-2-carbonyl)-amino]-2H-pyrazol-3-yl}-cyclobutyl ester | 366.3 (+) |
| 79 | (2-Diethylamino-ethyl)-carbamic acid cis-3-{5-[((R)-tetrahydro-furan-2-carbonyl)-amino]-2H-pyrazol-3-yl}-cyclobutyl ester | 394.3 (+) |
| 80 | [2-(2-Methyl-5-nitro-imidazol-1-yl)-ethyl]-carbamic acid cis-3-{5-[((R)-tetrahydro-furan-2-carbonyl)-amino]-1H-pyrazol-3-yl}-cyclobutyl ester | 448.2 (+) |
| 81 | [2-(cis-3-{5-[((R)-Tetrahydro-furan-2-carbonyl)-amino]-1H-pyrazol-3-yl}-cyclobutoxycarbonylamino)-ethyl]-carbamic acid benzyl ester | 472.2 (+) |
| 82 | (2-Acetylamino-ethyl)-carbamic acid cis-3-{5-[((R)-tetrahydro-furan-2-carbonyl)-amino]-1H-pyrazol-3-yl}-cyclobutyl ester | 378.1 (−) |
| 83 | [2-(5-Nitro-pyridin-2-ylamino)-ethyl]-carbamic acid cis-3-{5-[((R)-tetrahydro-furan-2-carbonyl)-amino]-1H-pyrazol-3-yl}-cyclobutyl ester | 460.2 (+) |
| 84 | (2-Fluoro-6-trifluoromethyl-benzyl)-carbamic acid cis-3-{5-[((R)-tetrahydro-furan-2-carbonyl)-amino]-1H-pyrazol-3-yl}-cyclobutyl ester | 471.2 (+) |
| 85 | (5-Methyl-furan-2-ylmethyl)-carbamic acid cis-3-{5-[((R)-tetrahydro-furan-2-carbonyl)-amino]-1H-pyrazol-3-yl}-cyclobutyl ester | 389.3 (+) |
| 86 | (2,2-Dimethyl-[1,3]dioxolan-4-ylmethyl)-carbamic acid cis-3-{5-[((R)-tetrahydro-furan-2-carbonyl)-amino]-1H-pyrazol-3-yl}-cyclobutyl ester | 409.3 (+) |
| 87 | Thiophen-2-ylmethyl-carbamic acid cis-3-{5-[((R)-tetrahydro-furan-2-carbonyl)-amino]-1H-pyrazol-3-yl}-cyclobutyl ester | 391.2 (+) |

| Example | Name | MS (M + H)+ or MS (M − H)− |
|---|---|---|
| 88 | [2-(Pyridin-2-ylamino)-ethyl]-carbamic acid cis-3-{5-[((R)-tetrahydro-furan-2-carbonyl)-amino]-1H-pyrazol-3-yl}-cyclobutyl ester | 413.2 (−) |
| 89 | [2-(4-Trifluoromethyl-pyridin-2-ylamino)-ethyl]-carbamic acid cis-3-{5-[((R)-tetrahydro-furan-2-carbonyl)-amino]-2H-pyrazol-3-yl}-cyclobutyl ester | 483.2 (+) |
| 90 | (1-Methyl-1H-imidazol-2-ylmethyl)-carbamic acid cis-3-{5-[((R)-tetrahydro-furan-2-carbonyl)-amino]-2H-pyrazol-3-yl}-cyclobutyl ester | 389.4 (+) |
| 91 | (7-Methyl-imidazo[1,2-a]pyridin-2-ylmethyl)-carbamic acid cis-3-{5-[((R)-tetrahydro-furan-2-carbonyl)-amino]-2H-pyrazol-3-yl}-cyclobutyl ester | 437.2 (−) |
| 92 | (2-Imidazol-1-yl-ethyl)-carbamic acid cis-3-{5-[((R)-tetrahydro-furan-2-carbonyl)-amino]-2H-pyrazol-3-yl}-cyclobutyl ester | 389.4 (+) |
| 93 | (1H-Indol-2-ylmethyl)-carbamic acid cis-3-{5-[((R)-tetrahydro-furan-2-carbonyl)-amino]-2H-pyrazol-3-yl}-cyclobutyl ester | 424.3 (+) |
| 94 | [2-(2-Oxo-pyrrolidin-1-yl)-ethyl]-carbamic acid cis-3-{5-[((R)-tetrahydro-furan-2-carbonyl)-amino]-2H-pyrazol-3-yl}-cyclobutyl ester | 406.3 (+) |
| 95 | (2-Chloro-6-fluoro-benzyl)-carbamic acid cis-3-{5-[(tetrahydro-pyran-4-carbonyl)-amino]-2H-pyrazol-3-yl}-cyclobutyl ester | 451.1 (+) |
| 96 | (2-Methyl-benzyl)-carbamic acid cis-3-{5-[(tetrahydro-pyran-4-carbonyl)-amino]-2H-pyrazol-3-yl}-cyclobutyl ester | 413.2 (+) |
| 97 | (4-Chloro-benzyl)-carbamic acid cis-3-{5-[(tetrahydro-pyran-4-carbonyl)-amino]-2H-pyrazol-3-yl}-cyclobutyl ester | 433.2 (+) |
| 98 | (2-Fluoro-3-trifluoromethyl-benzyl)-carbamic acid cis-3-{5-[(tetrahydro-pyran-4-carbonyl)-amino]-2H-pyrazol-3-yl}-cyclobutyl ester | 485.2 (+) |
| 99 | (4-Fluoro-benzyl)-carbamic acid cis-3-{5-[((R)-tetrahydro-furan-2-carbonyl)-amino]-2H-pyrazol-3-yl}-cyclobutyl ester | 403.2 (+) |
| 100 | (3,4-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 101 | (4-Fluoro-2-trifluoromethyl-benzyl)-carbamic acid cis-3-{5-[((R)-tetrahydro-furan-2-carbonyl)-amino]-2H-pyrazol-3-yl}-cyclobutyl ester | 471.2 (+) |
| 102 | (2,4,5-Trifluoro-benzyl)-carbamic acid cis-3-{5-[((R)-tetrahydro-furan-2-carbonyl)-amino]-2H-pyrazol-3-yl}-cyclobutyl ester | 439.2 (+) |
| 103 | (4-Fluoro-3-trifluoromethyl-benzyl)-carbamic acid cis-3-{5-[((R)-tetrahydro-furan-2-carbonyl)-amino]-2H-pyrazol-3-yl}-cyclobutyl ester | 471.2 (+) |
| 104 | (3,4,5-Trifluoro-benzyl)-carbamic acid cis-3-{5-[((R)-tetrahydro-furan-2-carbonyl)-amino]-2H-pyrazol-3-yl}-cyclobutyl ester | 439.2 (+) |
| 105 | (2,5-Dichloro-benzyl)-carbamic acid cis-3-{5-[((R)-tetrahydro-furan-2-carbonyl)-amino]-2H-pyrazol-3-yl}-cyclobutyl ester | 453.1 (+) |
| 106 | (3,4-Dichloro-benzyl)-carbamic acid cis-3-{5-[((R)-tetrahydro-furan-2-carbonyl)-amino]-2H-pyrazol-3-yl}-cyclobutyl ester | 453.1 (+) |
| 107 | (5-Chloro-2-methyl-benzyl)-carbamic acid cis-3-{5-[((R)-tetrahydro-furan-2-carbonyl)-amino]-2H-pyrazol-3-yl}-cyclobutyl ester | 433.3 (+) |
| 108 | (2-Chloro-6-fluoro-benzyl)-carbamic acid cis-3-(5-isobutyrylamino-2H-pyrazol-3-yl)-cyclobutyl ester | 409.1 (+) |
| 109 | (2-Trifluoromethyl-benzyl)-carbamic acid cis-3-(5-isobutyrylamino-2H-pyrazol-3-yl)-cyclobutyl ester | 425.1 (+) |
| 110 | (2-Fluoro-6-trifluoromethyl-benzyl)-carbamic acid cis-3-(5-isobutyrylamino-2H-pyrazol-3-yl)-cyclobutyl ester | 443.2 (+) |
| 111 | (2,6-Difluoro-benzyl)-carbamic acid cis-3-(5-isobutyrylamino-2H-pyrazol-3-yl)-cyclobutyl ester | 393.2 (+) |
| 112 | (2-Chloro-benzyl)-carbamic acid cis-3-(5-isobutyrylamino-2H-pyrazol-3-yl)-cyclobutyl ester | 391.2 (+) |
| 113 | (4-Chloro-benzyl)-carbamic acid cis-3-(5-isobutyrylamino-2H-pyrazol-3-yl)-cyclobutyl ester | 391.2 (+) |
| 114 | (2-Phenyl-propyl)-carbamic acid cis-3-(5-isobutyrylamino-2H-pyrazol-3-yl)-cyclobutyl ester | 385.3 (+) |
| 115 | (2-Fluoro-3-trifluoromethyl-benzyl)-carbamic acid cis-3-(5-isobutyrylamino-2H-pyrazol-3-yl)-cyclobutyl ester | 443.3 (+) |
| 116 | (2,4-Difluoro-benzyl)-carbamic acid cis-3-(5-isobutyrylamino-2H-pyrazol-3-yl)-cyclobutyl ester | 393.1 (+) |
| 117 | (2-Phenoxy-ethyl)-carbamic acid cis-3-(5-isobutyrylamino-2H-pyrazol-3-yl)-cyclobutyl ester | 387.1 (+) |
| 118 | (2-Phenylamino-ethyl)-carbamic acid cis-3-(5-isobutyrylamino-2H-pyrazol-3-yl)-cyclobutyl ester | 386.3 (+) |
| 119 | Benzyl-methyl-carbamic acid cis-3-(5-isobutyrylamino-2H-pyrazol-3-yl)-cyclobutyl ester | 371.2 (+) |
| 120 | Cyclohexylmethyl-carbamic acid cis-3-(5-isobutyrylamino-2H-pyrazol-3-yl)-cyclobutyl ester | 363.3 (+) |
| 121 | [2-(2-Methyl-pyridin-3-yl)-ethyl]-carbamic acid cis-3-{5-[((R)-tetrahydro-furan-2-carbonyl)-amino]-2H-pyrazol-3-yl}-cyclobutyl ester | 414.3 (+) |
| 122 | [2-(6-Methyl-pyridin-3-yl)-ethyl]-carbamic acid cis-3-{5-[((R)-tetrahydro-furan-2-carbonyl)-amino]-2H-pyrazol-3-yl}-cyclobutyl ester | 414.3 (+) |
| 123 | (3-Fluoro-benzyl)-carbamic acid cis-3-{5-[((R)-tetrahydro-furan-2-carbonyl)-amino]-2H-pyrazol-3-yl}-cyclobutyl ester | 403.2 (+) |
| 124 | (3,5-Difluoro-benzyl)-carbamic acid cis-3-{5-[((R)-tetrahydro-furan-2-carbonyl)-amino]-2H-pyrazol-3-yl}-cyclobutyl ester | 421.2 (+) |
| 125 | (3-Fluoro-5-trifluoromethyl-benzyl)-carbamic acid cis-3-{5-[((R)-tetrahydro-furan-2-carbonyl)-amino]-2H-pyrazol-3-yl}-cyclobutyl ester | 471.1 (+) |
| 126 | [2-(6-Methoxy-pyridin-3-yl)-ethyl]-carbamic acid cis-3-{5-[((R)-tetrahydro-furan-2-carbonyl)-amino]-2H-pyrazol-3-yl}-cyclobutyl ester | 430.2 (+) |

| Example | Name | MS (M + H)+ or MS (M − H)− |
|---|---|---|
| 127 | (3-Chloro-4-fluoro-benzyl)-carbamic acid cis-3-{5-[((R)-tetrahydro-furan-2-carbonyl)-amino]-2H-pyrazol-3-yl}-cyclobutyl ester | 437.4 (+) |
| 128 | Dimethyl-carbamic acid cis-3-(5-isobutyrylamino-2H-pyrazol-3-yl)-cyclobutyl ester | 293.2 (−) |
| 129 | Methyl-carbamic acid cis-3-(5-isobutyrylamino-2H-pyrazol-3-yl)-cyclobutyl ester | 281.3 (+) |
| 130 | Isopropyl-carbamic acid cis-3-(5-isobutyrylamino-2H-pyrazol-3-yl)-cyclobutyl ester | 309.4 (+) |
| 131 | Piperidine-1-carboxylic acid cis-3-(5-isobutyrylamino-2H-pyrazol-3-yl)-cyclobutyl ester | 335.4 (+) |
| 132 | Pyrrolidine-1-carboxylic acid cis-3-(5-isobutyrylamino-2H-pyrazol-3-yl)-cyclobutyl ester | 321.4 (+) |
| 133 | Butyl-carbamic acid cis-3-(5-isobutyrylamino-2H-pyrazol-3-yl)-cyclobutyl ester | 323.3 (+) |
| 134 | Propyl-carbamic acid cis-3-(5-isobutyrylamino-2H-pyrazol-3-yl)-cyclobutyl ester | 309.2 (+) |
| 135 | (2,2-Dimethyl-propyl)-carbamic acid cis-3-(5-isobutyrylamino-2H-pyrazol-3-yl)-cyclobutyl ester | 337.3 (+) |
| 136 | Isobutyl-carbamic acid cis-3-(5-isobutyrylamino-2H-pyrazol-3-yl)-cyclobutyl ester | 323.3 (+) |
| 137 | Morpholine-4-carboxylic acid cis-3-(5-isobutyrylamino-2H-pyrazol-3-yl)-cyclobutyl ester | 337.2 (+) |
| 138 | (Tetrahydro-pyran-4-ylmethyl)-carbamic acid cis-3-(5-isobutyrylamino-2H-pyrazol-3-yl)-cyclobutyl ester | 365.4 (+) |
| 139 | (2,2-Dimethyl-tetrahydro-pyran-4-yl)-carbamic acid cis-3-(5-isobutyrylamino-2H-pyrazol-3-yl)-cyclobutyl ester | 379.4 (+) |
| 140 | (Tetrahydro-furan-3-yl)-carbamic acid cis-3-(5-isobutyrylamino-2H-pyrazol-3-yl)-cyclobutyl ester | 337.3 (+) |
| 141 | Cyclohexyl-carbamic acid cis-3-(5-isobutyrylamino-2H-pyrazol-3-yl)-cyclobutyl ester | 349.3 (+) |
| 142 | (2-Methyl-butyl)-carbamic acid cis-3-(5-isobutyrylamino-2H-pyrazol-3-yl)-cyclobutyl ester | 337.3 (+) |
| 143 | Cyclopentyl-carbamic acid cis-3-(5-isobutyrylamino-2H-pyrazol-3-yl)-cyclobutyl ester | 335.3 (+) |
| 144 | (2-Ethyl-butyl)-carbamic acid cis-3-(5-isobutyrylamino-2H-pyrazol-3-yl)-cyclobutyl ester | 351.3 (+) |
| 145 | Cyclobutyl-carbamic acid cis-3-(5-isobutyrylamino-2H-pyrazol-3-yl)-cyclobutyl ester | 321.2 (+) |
| 146 | Azetidine-1-carboxylic acid cis-3-(5-isobutyrylamino-2H-pyrazol-3-yl)-cyclobutyl ester | 307.2 (+) |
| 147 | (3,4,5,6-Tetrahydro-2H-[1,2']bipyridinyl-3-ylmethyl)-carbamic acid cis-3-(5-isobutyrylamino-2H-pyrazol-3-yl)-cyclobutyl ester | 441.2 (+) |
| 148 | (2,2-Diphenyl-ethyl)-carbamic acid cis-3-(5-isobutyrylamino-2H-pyrazol-3-yl)-cyclobutyl ester | 447.2 (+) |
| 149 | (1-Benzyl-piperidin-4-yl)-carbamic acid cis-3-(5-isobutyrylamino-2H-pyrazol-3-yl)-cyclobutyl ester | 440.2 (+) |
| 150 | ((S)-1-Benzyl-pyrrolidin-3-yl)-carbamic acid cis-3-(5-isobutyrylamino-2H-pyrazol-3-yl)-cyclobutyl ester | 426.2 (+) |
| 151 | ((R)-1-Benzyl-pyrrolidin-3-yl)-carbamic acid cis-3-(5-isobutyrylamino-2H-pyrazol-3-yl)-cyclobutyl ester | 426.2 (+) |
| 152 | Pyridin-2-ylmethyl-carbamic acid cis-3-[5-(2-phenyl-butyrylamino)-2H-pyrazol-3-yl]-cyclobutyl ester | 434.1 (+) |
| 153 | Morpholine-4-carboxylic acid cis-3-[5-(2-phenyl-butyrylamino)-2H-pyrazol-3-yl]-cyclobutyl ester | 413.2 (+) |
| 154 | Dimethyl-carbamic acid cis-3-[5-(2-phenyl-butyrylamino)-2H-pyrazol-3-yl]-cyclobutyl ester | 371.2 (+) |
| 155 | Methyl-carbamic acid cis-3-[5-(2-phenyl-butyrylamino)-2H-pyrazol-3-yl]-cyclobutyl ester | 357.2 (+) |
| 156 | Ethyl-methyl-carbamic acid cis-3-[5-(2-phenyl-butyrylamino)-2H-pyrazol-3-yl]-cyclobutyl ester | 385.2 (+) |
| 157 | Isobutyl-carbamic acid cis-3-[5-(2-phenyl-butyrylamino)-2H-pyrazol-3-yl]-cyclobutyl ester | 399.2 (+) |
| 158 | Ethyl-carbamic acid cis-3-[5-(2-phenyl-butyrylamino)-2H-pyrazol-3-yl]-cyclobutyl ester | 371.2 (+) |
| 159 | Propyl-carbamic acid cis-3-[5-(2-phenyl-butyrylamino)-2H-pyrazol-3-yl]-cyclobutyl ester | 385.2 (+) |
| 160 | Propyl-carbamic acid cis-3-[5-(2-methyl-2-phenyl-propionylamino)-2H-pyrazol-3-yl]-cyclobutyl ester | 385.2 (+) |
| 161 | (Tetrahydro-pyran-4-ylmethyl)-carbamic acid cis-3-[5-(2-methyl-2-phenyl-propionylamino)-2H-pyrazol-3-yl]-cyclobutyl ester | 441.4 (+) |
| 162 | Pyridin-2-ylmethyl-carbamic acid cis-3-[5-(2-methyl-2-phenyl-propionylamino)-2H-pyrazol-3-yl]-cyclobutyl ester | 434.3 (+) |
| 163 | Ethyl-methyl-carbamic acid cis-3-[5-(2-methyl-2-phenyl-propionylamino)-2H-pyrazol-3-yl]-cyclobutyl ester | 385.4 (+) |
| 164 | Isobutyl-carbamic acid cis-3-[5-(2-methyl-2-phenyl-propionylamino)-2H-pyrazol-3-yl]-cyclobutyl ester | 399.2 (+) |
| 165 | Benzyl-carbamic acid cis-3-[5-(2-methyl-2-phenyl-propionylamino)-2H-pyrazol-3-yl]-cyclobutyl ester | 433.2 (+) |
| 166 | (2-Methoxy-benzyl)-carbamic acid cis-3-[5-(2-methyl-2-phenyl-propionylamino)-2H-pyrazol-3-yl]-cyclobutyl ester | 463.3 (+) |
| 167 | (2-Methyl-benzyl)-carbamic acid cis-3-[5-(2-methyl-2-phenyl-propionylamino)-2H-pyrazol-3-yl]-cyclobutyl ester | 447.4 (+) |
| 168 | (2-Fluoro-benzyl)-carbamic acid cis-3-[5-(2-methyl-2-phenyl-propionylamino)-2H-pyrazol-3-yl]-cyclobutyl ester | 451.4 (+) |
| 169 | (2,6-Difluoro-benzyl)-carbamic acid cis-3-[5-(2-methyl-2-phenyl-propionylamino)-2H-pyrazol-3-yl]-cyclobutyl ester | 469.4 (+) |
| 170 | (2-Trifluoromethyl-benzyl)-carbamic acid 3-[5-(2-methyl-2-phenyl-propionylamino)-2H-pyrazol-3-yl]-cyclobutyl ester | 501.5 (+) |
| 171 | Ethyl-carbamic acid cis-3-(5-isobutyrylamino-2H-pyrazol-3-yl)-cyclobutyl ester | 295.3 (+) |

EXAMPLE 172

(Tetrahydro-pyran-4-ylmethyl)-carbamic acid cis-3-[5-(2,2-dimethyl-propionylamino)-1H-pyrazol-3-yl]-cyclobutyl ester A solution of imidazole-1-carboxylic acid cis-3-[5-(2,2-dimethyl-propionylamino)-2H-pyrazol-3-yl]-cyclobutyl ester (200 mg) and C-(tetrahydro-pyran-4-yl)-methylamine (83 mg) in EtOAc was stirred at 70° C. overnight. After cooling, the isolated by silica gel chromatography. MS (M+H)$^+$=379.3.

The following compounds were prepared in a manner analogous to that described in Example 172 using appropriate starting materials. Amine starting materials that were obtained in the form of an acid addition salt were neutralized in situ by the addition of excess Et$_3$N. For Examples denoted with an asterisk, the reaction was heated in a microwave apparatus (150° C., 35 min), rather than at reflux.

| Example | Name | MS (M + H)$^+$ or MS (M − H)$^-$ |
|---|---|---|
| 173 | Benzyl-carbamic acid cis-3-[5-(2,2-dimethyl-propionylamino)-2H-pyrazol-3-yl]-cyclobutyl ester | 371.3 (+) |
| 174* | (4-Fluoro-benzyl)-carbamic acid cis-3-[5-(2,2-dimethyl-propionylamino)-2H-pyrazol-3-yl]-cyclobutyl ester | 389.2 (+) |
| 175 | (4-Methoxy-benzyl)-carbamic acid cis-3-[5-(2,2-dimethyl-propionylamino)-2H-pyrazol-3-yl]-cyclobutyl ester | 401.3 (+) |
| 176* | (2-Fluoro-benzyl)-carbamic acid cis-3-[5-(2,2-dimethyl-propionylamino)-2H-pyrazol-3-yl]-cyclobutyl ester | 389.2 (+) |
| 177* | (3-Fluoro-benzyl)-carbamic acid cis-3-[5-(2,2-dimethyl-propionylamino)-2H-pyrazol-3-yl]-cyclobutyl ester | 389.2 (+) |
| 178 | Benzyl-carbamic acid cis-3-{5-[(1-methyl-cyclohexanecarbonyl)-amino]-1H-pyrazol-3-yl}-cyclobutyl ester | 409.2 (−) |
| 179 | (2-Chloro-benzyl)-carbamic acid cis-3-{5-[(1-methyl-cyclohexanecarbonyl)-amino]-1H-pyrazol-3-yl}-cyclobutyl ester | 443.2 (−) |
| 180 | (2-Methoxy-2-methyl-propyl)-carbamic acid cis-3-[5-(2,2-dimethyl-propionylamino)-2H-pyrazol-3-yl]-cyclobutyl ester | 367.3 (+) |
| 181 | (3,4-Dihydro-2H-pyran-2-ylmethyl)-carbamic acid cis-3-[5-(2,2-dimethyl-propionylamino)-1H-pyrazol-3-yl]-cyclobutyl ester | 377.3 (+) |
| 182 | (2-Methoxy-benzyl)-carbamic acid cis-3-[5-(2,2-dimethyl-propionylamino)-1H-pyrazol-3-yl]-cyclobutyl ester | 401.3 (+) |
| 183 | (3-Methoxy-benzyl)-carbamic acid cis-3-[5-(2,2-dimethyl-propionylamino)-1H-pyrazol-3-yl]-cyclobutyl ester | 401.3 (+) |
| 184 | (2-Methoxy-ethyl)-carbamic acid cis-3-[5-(2,2-dimethyl-propionylamino)-1H-pyrazol-3-yl]-cyclobutyl ester | 339.2 (+) |
| 185 | Butyl-carbamic acid cis-3-[5-(2,2-dimethyl-propionylamino)-1H-pyrazol-3-yl]-cyclobutyl ester | 337.3 (+) |
| 186 | Isobutyl-carbamic acid cis-3-[5-(2,2-dimethyl-propionylamino)-1H-pyrazol-3-yl]-cyclobutyl ester | 337.3 (+) |
| 187 | Benzyl-methyl-carbamic acid cis-3-[5-(2,2-dimethyl-propionylamino)-1H-pyrazol-3-yl]-cyclobutyl ester | 385.3 (+) |
| 188 | (Tetrahydro-furan-2-ylmethyl)-carbamic acid cis-3-[5-(2,2-dimethyl-propionylamino)-1H-pyrazol-3-yl]-cyclobutyl ester | 365.2 (+) |
| 189 | (2-Phenylamino-ethyl)-carbamic acid cis-3-[5-(2,2-dimethyl-propionylamino)-1H-pyrazol-3-yl]-cyclobutyl ester | 400.3 (+) |
| 190 | (2,4-Dichloro-benzyl)-carbamic acid cis-3-{5-[(1-methyl-cyclohexanecarbonyl)-amino]-1H-pyrazol-3-yl}-cyclobutyl ester | 479.1 (+) |
| 191 | (2-Trifluoromethyl-benzyl)-carbamic acid cis-3-{5-[(1-methyl-cyclohexanecarbonyl)-amino]-1H-pyrazol-3-yl}-cyclobutyl ester | 479.2 (+) |
| 192 | (2,4-Difluoro-benzyl)-carbamic acid cis-3-{5-[(1-methyl-cyclohexanecarbonyl)-amino]-1H-pyrazol-3-yl}-cyclobutyl ester | 447.2 (+) |
| 193 | Pyridin-2-ylmethyl-carbamic acid cis-3-{5-[(1-methyl-cyclohexanecarbonyl)-amino]-1H-pyrazol-3-yl}-cyclobutyl ester | 412.2 (+) |
| 194 | (R)-3-Propoxy-pyrrolidine-1-carboxylic acid cis-3-[5-(2,2-dimethyl-propionylamino)-2H-pyrazol-3-yl]-cyclobutyl ester | 393.3 (+) |
| 195 | Isochroman-1-ylmethyl-carbamic acid cis-3-[5-(2,2-dimethyl-propionylamino)-2H-pyrazol-3-yl]-cyclobutyl ester | 427.3 (+) |
| 196 | [2-(2-Chloro-phenoxy)-propyl]-carbamic acid cis-3-[5-(2,2-dimethyl-propionylamino)-2H-pyrazol-3-yl]-cyclobutyl ester | 449.2 (+) |
| 197 | (2,2-Dimethyl-propyl)-carbamic acid cis-3-[5-(2,2-dimethyl-propionylamino)-2H-pyrazol-3-yl]-cyclobutyl ester | 351.2 (+) |
| 198 | Piperazine-1,4-dicarboxylic acid cis-3-[5-(2,2-dimethyl-propionylamino)-2H-pyrazol-3-yl]-cyclobutyl ester ethyl ester | 422.2 (+) |
| 199 | 4-Pyridin-2-yl-piperazine-1-carboxylic acid cis-3-[5-(2,2-dimethyl-propionylamino)-2H-pyrazol-3-yl]-cyclobutyl ester | 427.2 (+) |
| 200 | (2R,6S)-2,6-Dimethyl-morpholine-4-carboxylic acid cis-3-[5-(2,2-dimethyl-propionylamino)-2H-pyrazol-3-yl]-cyclobutyl ester | 379.2 (+) |
| 201 | (S)-3-Methoxy-pyrrolidine-1-carboxylic acid cis-3-[5-(2,2-dimethyl-propionylamino)-2H-pyrazol-3-yl]-cyclobutyl ester | 365.2 (+) |
| 202 | (2-Trifluoromethoxy-benzyl)-carbamic acid cis-3-[5-(2,2-dimethyl-propionylamino)-2H-pyrazol-3-yl]-cyclobutyl ester | 455.1 (+) |
| 203 | 4-Phenyl-piperazine-1-carboxylic acid cis-3-[5-(2,2-dimethyl-propionylamino)-2H-pyrazol-3-yl]-cyclobutyl ester | 426.3 (+) |
| 204 | 3-Pyridin-2-yl-pyrrolidine-1-carboxylic acid cis-3-[5-(2,2-dimethyl-propionylamino)-2H-pyrazol-3-yl]-cyclobutyl ester | 412.3 (+) |
| 205 | [2-(Pyridin-3-yloxy)-propyl]-carbamic acid cis-3-[5-(2,2-dimethyl-propionylamino)-2H-pyrazol-3-yl]-cyclobutyl ester | 416.3 (+) |
| 206 | 3-(Acetyl-methyl-amino)-pyrrolidine-1-carboxylic acid cis-3-[5-(2,2-dimethyl-propionylamino)-2H-pyrazol-3-yl]-cyclobutyl ester | 406.2 (+) |

| Example | Name | MS (M + H)+ or MS (M − H)− |
|---|---|---|
| 207 | (4-Fluoro-2-trifluoromethyl-benzyl)-carbamic acid cis-3-{5-[(1-methyl-cyclohexanecarbonyl)-amino]-1H-pyrazol-3-yl}-cyclobutyl ester | 497.0 (+) |
| 208 | (3,4-Dichloro-benzyl)-carbamic acid cis-3-{5-[(1-methyl-cyclohexanecarbonyl)-amino]-1H-pyrazol-3-yl}-cyclobutyl ester | 480.2 (+) |
| 209 | (3,5-Difluoro-benzyl)-carbamic acid cis-3-{5-[(1-methyl-cyclohexanecarbonyl)-amino]-1H-pyrazol-3-yl}-cyclobutyl ester | 447.3 (+) |
| 210 | (3-Chloro-2-methyl-benzyl)-carbamic acid cis-3-{5-[(1-methyl-cyclohexanecarbonyl)-amino]-1H-pyrazol-3-yl}-cyclobutyl ester | 459.2 (+) |
| 211 | (4-Isopropyl-benzyl)-carbamic acid cis-3-{5-[(1-methyl-cyclohexanecarbonyl)-amino]-1H-pyrazol-3-yl}-cyclobutyl ester | 453.3 (+) |
| 212 | (2,6-Difluoro-benzyl)-carbamic acid cis-3-{5-[(1-methyl-cyclohexanecarbonyl)-amino]-1H-pyrazol-3-yl}-cyclobutyl ester | 447.2 (+) |
| 213 | (3-Chloro-benzyl)-carbamic acid cis-3-{5-[(1-methyl-cyclohexanecarbonyl)-amino]-1H-pyrazol-3-yl}-cyclobutyl ester | 445.1 (+) |
| 214 | (3-Fluoro-benzyl)-carbamic acid cis-3-{5-[(1-methyl-cyclohexanecarbonyl)-amino]-1H-pyrazol-3-yl}-cyclobutyl ester | 429.2 (+) |
| 215 | (5,7-Dimethyl-benzothiazol-2-yl)-carbamic acid cis-3-{5-[(1-methyl-cyclohexanecarbonyl)-amino]-1H-pyrazol-3-yl}-cyclobutyl ester | 482.2 (+) |
| 216 | Indan-1-yl-carbamic acid cis-3-[5-(2,2-dimethyl-propionylamino)-2H-pyrazol-3-yl]-cyclobutyl ester | 397.2 (+) |
| 217 | (1,2,3,4-Tetrahydro-naphthalen-1-yl)-carbamic acid cis-3-[5-(2,2-dimethyl-propionylamino)-2H-pyrazol-3-yl]-cyclobutyl ester | 411.2 (+) |
| 218 | (1-Phenyl-propyl)-carbamic acid cis-3-[5-(2,2-dimethyl-propionylamino)-2H-pyrazol-3-yl]-cyclobutyl ester | 399.2 (+) |
| 219 | ((S)-1-Phenyl-ethyl)-carbamic acid cis-3-[5-(2,2-dimethyl-propionylamino)-2H-pyrazol-3-yl]-cyclobutyl ester | 385.2 (+) |
| 220 | ((R)-1-Phenyl-ethyl)-carbamic acid cis-3-[5-(2,2-dimethyl-propionylamino)-2H-pyrazol-3-yl]-cyclobutyl ester | 385.2 (+) |

EXAMPLE 221

Methyl-pyridin-3-ylmethyl-carbamic acid cis-3-[5-(2,2-dimethyl-propionylamino)-2H-pyrazol-3-yl]-cyclobutyl ester Step A A solution of N-[2-tert-butyl-5-(3-oxo-cyclobutyl)-2H-pyrazol-3-yl]-2,2-dimethyl-propionamide (6.9 g) in TFA (47 mL) was heated at reflux for 29 h. The solution was cooled, concentrated, and the resulting residue was partitioned between $CH_2Cl_2$ and saturated aqueous $NaHCO_3$ solution. The organic layer was dried over $Na_2SO_4$ and concentrated to afford the product as a light yellow solid that was used without further purification.

Step B

A mixture of the product of Step A (2.7 g), di-tert-butyldicarbonate (3.6 g), $Et_3N$ (2.85 mL), and DMAP (63 mg) in $CH_2Cl_2$ was stirred at room temperature for 2 h. The solution was concentrated and the resulting residue dissolved in EtOAc. The solution was washed sequentially with saturated aqueous $NH_4Cl$ solution, water, and saturated aqueous NaCl solution. The organic layer was dried over $Na_2SO_4$ and concentrated to afford a mixture of carbamate isomers that was used without further purification.

Step C

Sodium borohydride (430 mg) was added to a solution of the product of Step B (4.8 g) in THF (34 mL) and EtOH (4.9 mL) at −78° C. After 10 min, the reaction mixture was warmed to 0° C. for 15 min. Excess hydride was quenched by the addition of saturated aqueous $NH_4Cl$ solution and the mixture was concentrated. The residue was dissolved in EtOAc and washed sequentially with saturated aqueous $NaHCO_3$ solution (2×), water, and saturated aqueous NaCl solution. The organic layer was dried over $Na_2SO_4$ and then was concentrated to afford the product as a yellow foam that was used without further purification.

Step D

The product of Step C (200 mg) was dissolved in $CH_2Cl_2$ and the resulting solution was cooled to 0° C. A solution of triphosgene (123 mg) in $CH_2Cl_2$ (0.5 mL) was added followed by pyridine (0.125 mL). The reaction solution was warmed to room temperature and, after an additional 1 h, methyl-pyridin-3-ylmethyl-amine (180 mg) was added. After an additional 1 h, the solution was concentrated, the resulting residue was dissolved in EtOAc, and the solution washed sequentially with saturated aqueous $NH_4Cl$ solution and water, dried over $Na_2SO_4$, and concentrated to afford the product carbamate as a mixture of isomers that was used without further purification.

Step E

A solution of the product of Step D (230 mg) in $CH_3CN$ was heated to 150° C. in a microwave apparatus for 5 min. The solution was concentrated and the resulting residue was purified by silica gel chromatography to afford the title compound as a white solid. MS (M−H)−=384.3.

The following compounds were prepared in a manner analogous to that described in Example 221 using appropriate starting materials.

| Example | Name | MS (M + H)+ or MS (M − H)− |
|---|---|---|
| 222 | tert-Butyl-carbamic acid cis-3-[5-(2,2-dimethyl-propionylamino)-2H-pyrazol-3-yl]-cyclobutyl ester | 337.1 (+) |
| 223 | (6-Methyl-pyridin-2-ylmethyl)-carbamic acid cis-3-[5-(2,2-dimethyl-propionylamino)-2H-pyrazol-3-yl]-cyclobutyl ester | 386.1 (+) |
| 224 | (3-Chloro-5-trifluoromethyl-pyridin-2-ylmethyl)-carbamic acid cis-3-[5-(2,2-dimethyl-propionylamino)-2H-pyrazol-3-yl]-cyclobutyl ester | 474 (+) |
| 225 | (1,1-Dimethyl-propyl)-carbamic acid cis-3-[5-(2,2-dimethyl-propionylamino)-2H-pyrazol-3-yl]-cyclobutyl ester | 351.3 (+) |
| 226 | [2-(4-Fluoro-phenyl)-1,1-dimethyl-ethyl]-carbamic acid cis-3-[5-(2,2-dimethyl-propionylamino)-2H-pyrazol-3-yl]-cyclobutyl ester | 431.3 (+) |

-continued

| Example | Name | MS (M + H)+ or MS (M − H)− |
|---|---|---|
| 227 | (1-Methyl-1-phenyl-ethyl)-carbamic acid cis-3-[5-(2,2-dimethyl-propionylamino)-2H-pyrazol-3-yl]-cyclobutyl ester | 399.3 (+) |
| 228 | Diethyl-carbamic acid cis-3-[5-(2,2-dimethyl-propionylamino)-2H-pyrazol-3-yl]-cyclobutyl ester | 337.3 (+) |
| 229 | (2,2,2-Trifluoro-ethyl)-carbamic acid cis-3-[5-(2,2-dimethyl-propionylamino)-2H-pyrazol-3-yl]-cyclobutyl ester | 363.2 (+) |
| 230 | tert-Butyl-methyl-carbamic acid cis-3-[5-(2,2-dimethyl-propionylamino)-1H-pyrazol-3-yl]-cyclobutyl ester | 351.3 (+) |
| 231 | (Tetrahydro-pyran-2-ylmethyl)-carbamic acid cis-3-[5-(2,2-dimethyl-propionylamino)-2H-pyrazol-3-yl]-cyclobutyl ester | 379.3 (+) |
| 232 | Methyl-propyl-carbamic acid cis-3-[5-(2,2-dimethyl-propionylamino)-2H-pyrazol-3-yl]-cyclobutyl ester | 337.2 (+) |
| 233 | Isobutyl-methyl-carbamic acid cis-3-[5-(2,2-dimethyl-propionylamino)-2H-pyrazol-3-yl]-cyclobutyl ester | 351.2 (+) |
| 234 | Cyclopropylmethyl-propyl-carbamic acid cis-3-[5-(2,2-dimethyl-propionylamino)-2H-pyrazol-3-yl]-cyclobutyl ester | 377.3 (+) |
| 235 | (2-Methoxy-ethyl)-methyl-carbamic acid cis-3-[5-(2,2-dimethyl-propionylamino)-2H-pyrazol-3-yl]-cyclobutyl ester | 353.2 (+) |
| 236 | Cyclohexyl-methyl-carbamic acid cis-3-[5-(2,2-dimethyl-propionylamino)-2H-pyrazol-3-yl]-cyclobutyl ester | 377.3 (+) |
| 237 | 2-Ethyl-piperidine-1-carboxylic acid cis-3-[5-(2,2-dimethyl-propionylamino)-2H-pyrazol-3-yl]-cyclobutyl ester | 377.3 (+) |
| 238 | (2-Cyano-ethyl)-cyclohexyl-carbamic acid cis-3-[5-(2,2-dimethyl-propionylamino)-2H-pyrazol-3-yl]-cyclobutyl ester | 416.2 (+) |
| 239 | Ethyl-isopropyl-carbamic acid cis-3-[5-(2,2-dimethyl-propionylamino)-2H-pyrazol-3-yl]-cyclobutyl ester | 351.2 (+) |
| 240 | (R)-2-Methoxymethyl-pyrrolidine-1-carboxylic acid cis-3-[5-(2,2-dimethyl-propionylamino)-2H-pyrazol-3-yl]-cyclobutyl ester | 379.2 (+) |
| 241 | Methyl-((R)-1-phenyl-ethyl)-carbamic acid cis-3-[5-(2,2-dimethyl-propionylamino)-2H-pyrazol-3-yl]-cyclobutyl ester | 399.2 (+) |
| 242 | Isopropyl-(2-methoxy-ethyl)-carbamic acid cis-3-[5-(2,2-dimethyl-propionylamino)-2H-pyrazol-3-yl]-cyclobutyl ester | 381.2 (+) |
| 243 | Methyl-(3-methyl-pyridin-2-ylmethyl)-carbamic acid cis-3-[5-(2,2-dimethyl-propionylamino)-2H-pyrazol-3-yl]-cyclobutyl ester | 398.3 (−) |
| 244 | Methyl-quinoxalin-2-ylmethyl-carbamic acid cis-3-[5-(2,2-dimethyl-propionylamino)-2H-pyrazol-3-yl]-cyclobutyl ester | 437.3 (+) |
| 245 | Methyl-quinolin-8-ylmethyl-carbamic acid cis-3-[5-(2,2-dimethyl-propionylamino)-2H-pyrazol-3-yl]-cyclobutyl ester | 436.3 (+) |
| 246 | Methyl-quinolin-6-ylmethyl-carbamic acid cis-3-[5-(2,2-dimethyl-propionylamino)-2H-pyrazol-3-yl]-cyclobutyl ester | 436.2 (+) |
| 247 | Methyl-quinolin-5-ylmethyl-carbamic acid cis-3-[5-(2,2-dimethyl-propionylamino)-2H-pyrazol-3-yl]-cyclobutyl ester | 436.2 (+) |
| 248 | Methyl-pyridin-2-ylmethyl-carbamic acid cis-3-[5-(2,2-dimethyl-propionylamino)-2H-pyrazol-3-yl]-cyclobutyl ester | 386.2 (+) |
| 249 | Methyl-pyridin-4-ylmethyl-carbamic acid cis-3-[5-(2,2-dimethyl-propionylamino)-2H-pyrazol-3-yl]-cyclobutyl ester | 386.2 (+) |
| 250 | Methyl-(1-pyridin-2-yl-ethyl)-carbamic acid cis-3-[5-(2,2-dimethyl-propionylamino)-2H-pyrazol-3-yl]-cyclobutyl ester | 400.1 (+) |
| 251 | (1-Phenyl-cyclopentyl)-carbamic acid cis-3-[5-(2,2-dimethyl-propionylamino)-2H-pyrazol-3-yl]-cyclobutyl ester | 425.2 (+) |
| 252 | Isobutyl-carbamic acid cis-3-{5-[(2-methyl-tetrahydro-furan-2-carbonyl)-amino]-2H-pyrazol-3-yl}-cyclobutyl ester | 365.2 (+) |
| 253 | Isobutyl-carbamic acid cis-3-{5-[(4-methyl-tetrahydro-pyran-4-carbonyl)-amino]-2H-pyrazol-3-yl}-cyclobutyl ester | 379.4 (+) |
| 254 | tert-Butyl-carbamic acid cis-3-{5-[(2-methyl-tetrahydro-furan-2-carbonyl)-amino]-2H-pyrazol-3-yl}-cyclobutyl ester | 365.3 (+) |
| 255 | Dimethyl-carbamic acid cis-3-{5-[(2-methyl-tetrahydro-furan-2-carbonyl)-amino]-2H-pyrazol-3-yl}-cyclobutyl ester | 337.2 (+) |
| 256 | tert-Butyl-carbamic acid cis-3-{5-[(4-methyl-tetrahydro-pyran-4-carbonyl)-amino]-2H-pyrazol-3-yl}-cyclobutyl ester | 379.4 (+) |
| 257 | Dimethyl-carbamic acid cis-3-{5-[(4-methyl-tetrahydro-pyran-4-carbonyl)-amino]-2H-pyrazol-3-yl}-cyclobutyl ester | 351.4 (+) |
| 258 | Benzyl-carbamic acid cis-3-{5-[(4-methyl-tetrahydro-pyran-4-carbonyl)-amino]-2H-pyrazol-3-yl}-cyclobutyl ester | 413.4 (+) |
| 259 | Pyridin-2-ylmethyl-carbamic acid cis-3-{5-[(4-methyl-tetrahydro-pyran-4-carbonyl)-amino]-2H-pyrazol-3-yl}-cyclobutyl ester | 414.5 (+) |

The following compounds were prepared in a manner analogous to that described in Example 221 using appropriate starting materials, except Step E employed DMSO as solvent, rather than $CH_3CN$.

| Example | Name | MS (M + H)+ |
|---|---|---|
| 260 | Propyl-carbamic acid cis-3-[5-(2-methyl-2-pyridin-2-yl-propionylamino)-2H-pyrazol-3-yl]-cyclobutyl ester | 386.3 |
| 261 | Pyridin-2-ylmethyl-carbamic acid cis-3-[5-(2-methyl-2-pyridin-2-yl-propionylamino)-2H-pyrazol-3-yl]-cyclobutyl ester | 435.2 |
| 262 | Isopropyl-carbamic acid cis-3-[5-(2-methyl-2-pyridin-2-yl-propionylamino)-2H-pyrazol-3-yl]-cyclobutyl ester | 386.4 |

-continued

| Example | Name | MS (M + H)+ |
|---|---|---|
| 263 | Cyclobutyl-carbamic acid cis-3-[5-(2-methyl-2-pyridin-2-yl-propionylamino)-2H-pyrazol-3-yl]-cyclobutyl ester | 398.3 |
| 264 | Methyl-propyl-carbamic acid cis-3-[5-(2-methyl-2-pyridin-2-yl-propionylamino)-2H-pyrazol-3-yl]-cyclobutyl ester | 400.3 |
| 265 | ((S)-1-Phenyl-ethyl)-carbamic acid cis-3-[5-(2-methyl-2-pyridin-2-yl-propionylamino)-2H-pyrazol-3-yl]-cyclobutyl ester | 448.3 |
| 266 | ((R)-1-Phenyl-ethyl)-carbamic acid cis-3-[5-(2-methyl-2-pyridin-2-yl-propionylamino)-2H-pyrazol-3-yl]-cyclobutyl ester | 448.3 |
| 267 | Isopropyl-methyl-carbamic acid cis-3-[5-(2-methyl-2-pyridin-2-yl-propionylamino)-2H-pyrazol-3-yl]-cyclobutyl ester | 400.3 |
| 268 | Methyl-carbamic acid cis-3-[5-(2-methyl-2-pyridin-2-yl-propionylamino)-2H-pyrazol-3-yl]-cyclobutyl ester | 358.2 |
| 269 | (2-Methoxy-ethyl)-carbamic acid cis-3-[5-(2-methyl-2-pyridin-2-yl-propionylamino)-2H-pyrazol-3-yl]-cyclobutyl ester | 402.3 |
| 270 | Diethyl-carbamic acid cis-3-[5-(2-methyl-2-pyridin-2-yl-propionylamino)-2H-pyrazol-3-yl]-cyclobutyl ester | 400.3 |
| 271 | tert-Butyl-carbamic acid cis-3-[5-(2-methyl-2-pyridin-2-yl-propionylamino)-2H-pyrazol-3-yl]-cyclobutyl ester | 400.3 |
| 272 | (1-Methyl-1-phenyl-ethyl)-carbamic acid cis-3-[5-(2-methyl-2-pyridin-2-yl-propionylamino)-2H-pyrazol-3-yl]-cyclobutyl ester | 462.4 |
| 273 | Ethyl-methyl-carbamic acid cis-3-[5-(2-methyl-2-pyridin-2-yl-propionylamino)-2H-pyrazol-3-yl]-cyclobutyl ester | 386.3 |
| 275 | tert-Butyl-carbamic acid cis-3-[5-(cyclohexanecarbonyl-amino)-2H-pyrazol-3-yl]-cyclobutyl ester | 363.5 |
| 276 | Phenyl-carbamic acid cis-3-[5-(2,2-dimethyl-propionylamino)-2H-pyrazol-3-yl]-cyclobutyl ester | 357.3 |
| 277 | Methyl-pyridin-2-yl-carbamic acid cis-3-[5-(2,2-dimethyl-propionylamino)-2H-pyrazol-3-yl]-cyclobutyl ester | 372.3 |
| 278 | (6-Methyl-pyridin-2-yl)-carbamic acid cis-3-[5-(2,2-dimethyl-propionylamino)-2H-pyrazol-3-yl]-cyclobutyl ester | 372.3 |
| 279 | Methyl-phenyl-carbamic acid cis-3-[5-(2,2-dimethyl-propionylamino)-2H-pyrazol-3-yl]-cyclobutyl ester | 371.3 |
| 280 | Pyrimidin-2-yl-carbamic acid cis-3-[5-(2,2-dimethyl-propionylamino)-2H-pyrazol-3-yl]-cyclobutyl ester | 359.3 |
| 281 | Ethyl-carbamic acid cis-3-[5-(2-methyl-2-pyridin-2-yl-propionylamino)-2H-pyrazol-3-yl]-cyclobutyl ester | 372.3 |
| 282 | (2-Fluoro-benzyl)-carbamic acid cis-3-[5-(2-methyl-2-pyridin-2-yl-propionylamino)-2H-pyrazol-3-yl]-cyclobutyl ester | 452.2 |
| 283 | Pyrrolidine-1-carboxylic acid cis-3-[5-(2-methyl-2-pyridin-2-yl-propionylamino)-2H-pyrazol-3-yl]-cyclobutyl ester | 398.3 |
| 284 | Morpholine-4-carboxylic acid cis-3-[5-(2-methyl-2-pyridin-2-yl-propionylamino)-2H-pyrazol-3-yl]-cyclobutyl ester | 414.3 |
| 285 | (2,6-Difluoro-benzyl)-carbamic acid cis-3-[5-(2-methyl-2-pyridin-2-yl-propionylamino)-2H-pyrazol-3-yl]-cyclobutyl ester | 470.2 |
| 286 | Methyl-pyridin-2-ylmethyl-carbamic acid cis-3-[5-(2-methyl-2-pyridin-2-yl-propionylamino)-2H-pyrazol-3-yl]-cyclobutyl ester | 449.0 |
| 287 | tert-Butyl-methyl-carbamic acid cis-3-[5-(2-methyl-2-pyridin-2-yl-propionylamino)-2H-pyrazol-3-yl]-cyclobutyl ester | 414.4 |

EXAMPLE 274

Cyclopropylmethyl-carbamic acid 3-[5-(2-methyl-2-pyridin-2-yl-propionylamino)-2H-pyrazol-3-yl]-cyclobutyl ester A mixture of 5-(3-cyclopropylmethylcarbamoyloxy-cyclobutyl)-3-(2-methyl-2-pyridin-2-yl-propionylamino)-pyrazole-1-carboxylic acid tert-butyl ester and 3-(3-cyclopropylmethylcarbamoyloxy-cyclobutyl)-5-(2-methyl-2-pyridin-2-yl-propionylamino)-pyrazole-1-carboxylic acid tert-butyl ester (120 mg, prepared by procedures analogous to those described in Example 221, Steps A to E, using appropriate starting materials) was dissolved in TFA (0.19 mL) and CH$_2$Cl$_2$ (1.25 mL) at room temperature. After 4 h, the solution was diluted with EtOAc and the solution was washed sequentially with saturated aqueous NaHCO$_3$ solution (2×), water, and saturated aqueous NaCl solution. The organic layer was dried over Na$_2$SO$_4$ and concentrated. Purification of the residue by silica gel chromatography afforded the title compound as a solid. MS (M+H)$^+$=398.3.

The following compounds were prepared in a manner analogous to that described in Example 274 using appropriate starting materials.

EXAMPLE 288

2-Methyl-pyrrolidine-1-carboxylic acid cis-3-{5-[(tetrahydro-pyran-carbonyl)-amino]-2H-pyrazol-3-yl}-cyclobutyl ester Step A A mixture of 5-(cis-3-hydroxy-cyclobutyl)-3-[(tetrahydro-pyran-4-carbonyl)-amino]-pyrazole-1-carboxylic acid tert-butyl ester and 3-(cis-3-hydroxy-cyclobutyl)-5-[(tetrahydro-pyran-4-carbonyl)-amino]-pyrazole-1-carboxylic acid tert-butyl ester (120 mg, prepared by procedures analogous to those described in Example 221, Steps B to C, using appropriate starting materials), triphosgene (69 mg), and PS-DMAP resin (0.30 mmol) were stirred in CH$_2$Cl$_2$ (2 mL) at 0° C. After 60 min 2-methyl-pyrrolidine (0.10 mL) was added and the resulting mixture was stirred overnight. The resin was removed by filtration and the filtrate was concentrated to afford the product carbamate that was used without further purification.

Step B

A solution of the product of Step A (157 mg) in DMSO was heated at 150° C. in a microwave apparatus for 7 min. The solution was then purified by reversed-phase preparative HPLC to afford the title product as a solid. MS (M+H)$^+$ =377.2.

The following compounds were prepared in a manner analogous to that described in Example 288 using appropriate starting materials.

| Example | Name | MS (M + H)$^+$ or MS (M − H)$^-$ |
|---------|------|----------------------------------|
| 289 | tert-Butyl-carbamic acid cis-3-{5-[(tetrahydro-pyran-4-carbonyl)-amino]-2H-pyrazol-3-yl}-cyclobutyl ester | 363.2 (−) |
| 290 | (6-Methyl-pyridin-2-ylmethyl)-carbamic acid cis-3-{5-[(tetrahydro-pyran-4-carbonyl)-amino]-2H-pyrazol-3-yl}-cyclobutyl ester | 412.3 (−) |
| 291 | (1-Methyl-1-phenyl-ethyl)-carbamic acid cis-3-{5-[(tetrahydro-pyran-4-carbonyl)-amino]-2H-pyrazol-3-yl}-cyclobutyl ester | 427.2 (+) |
| 292 | Methyl-(3-methyl-pyridin-2-ylmethyl)-carbamic acid cis-3-{5-[(tetrahydro-pyran-4-carbonyl)-amino]-2H-pyrazol-3-yl}-cyclobutyl ester | 426.1 (−) |
| 293 | (2,2,2-Trifluoro-1-pyridin-2-yl-ethyl)-carbamic acid cis-3-{5-[(tetrahydro-pyran-4-carbonyl)-amino]-2H-pyrazol-3-yl}-cyclobutyl ester | 468.1 (+) |
| 294 | (2R,6S)-2,6-Dimethyl-morpholine-4-carboxylic acid cis-3-{5-[(tetrahydro-pyran-4-carbonyl)-amino]-2H-pyrazol-3-yl}-cyclobutyl ester | 407.2 (+) |
| 295 | 2-Pyridin-2-yl-pyrrolidine-1-carboxylic acid cis-3-{5-[(tetrahydro-pyran-4-carbonyl)-amino]-2H-pyrazol-3-yl}-cyclobutyl ester | 438.1 (−) |
| 296 | Methyl-pyridin-2-ylmethyl-carbamic acid cis-3-{5-[(tetrahydro-pyran-4-carbonyl)-amino]-2H-pyrazol-3-yl}-cyclobutyl ester | 414.2 (+) |
| 297 | Methyl-(1-pyridin-2-yl-ethyl)-carbamic acid cis-3-{5-[(tetrahydro-pyran-4-carbonyl)-amino]-2H-pyrazol-3-yl}-cyclobutyl ester | 426.1 (−) |
| 298 | 2-Methoxymethyl-pyrrolidine-1-carboxylic acid cis-3-{5-[(tetrahydro-pyran-4-carbonyl)-amino]-2H-pyrazol-3-yl}-cyclobutyl ester | 407.2 (+) |
| 299 | tert-Butyl-methyl-carbamic acid cis-3-{5-[(tetrahydro-pyran-4-carbonyl)-amino]-2H-pyrazol-3-yl}-cyclobutyl ester | 379.2 (+) |
| 300 | Benzyl-ethyl-carbamic acid cis-3-{5-[(tetrahydro-pyran-4-carbonyl)-amino]-2H-pyrazol-3-yl}-cyclobutyl ester | 427.2 (+) |

EXAMPLE 301

Isobutyl-carbamic acid cis-3-[5-(2-p-tolyl-acetylamino)-1H-pyrazol-3-yl]-cyclobutyl ester Step A A solution of 2-tert-butyl-5-(3,3-dimethoxy-cyclobutyl)-2H-pyrazol-3-ylamine (4.0 g), di-tert-butyl dicarbonate (10.4 g), Et$_3$N (6.6 mL), and DMAP (40 mg) in CH$_2$Cl$_2$ (60 mL) was stirred at room temperature for 3 days. The solution was concentrated to afford the bis-carbamoylated product as an oil that was used without further purification.

Step B

The product of Step A was converted into [2-tert-butyl-5-(cis-3-isobutylcarbamoyloxy-cyclobutyl)-2H-pyrazol-3-yl]-imidodicarboxylic acid di-tert-butyl ester using appropriate starting materials by procedures analogous to those described in Example 1, Steps B to C, and Example 9, Step A.

Step C

A solution of the product of Step B (4.5 g) in TFA (40 mL) was stirred at room temperature for 4 h. The solution was concentrated and the residue was dissolved in CHCl$_3$. The solution was washed sequentially with saturated aqueous NaHCO$_3$ solution and saturated aqueous NaCl solution. The organic layer was dried over Na$_2$SO$_4$ and concentrated. Purification of the residue by silica gel chromatography afforded the amine product as an oil.

Step D

To p-tolyl-acetic acid (0.18 mmol) was added sequentially: the product of Step C (1 mL of a 0.16 M solution in EtOAc), 1-propanephosphonic acid cyclic anhydride (1 mL of a 0.36 M solution in EtOAc), and Et$_3$N (1 mL of a 0.72 M solution in EtOAc). The resulting solution was heated at reflux overnight and concentrated to afford a residue that used without purification in the next step.

Step E

The product of Step D was dissolved in TFA (2 mL) and the solution was heated at reflux overnight. The solution was concentrated and the residue purified by reversed-phase preparative HPLC to afford the title product. MS (M+H)$^+$=385.4.

The following compounds were prepared in a manner analogous to that described in Example 301 using appropriate starting materials.

| Example | Name | MS (M + H)$^+$ |
|---------|------|----------------|
| 302 | Isobutyl-carbamic acid cis-3-[5-(3-methyl-2-phenyl-butyrylamino)-1H-pyrazol-3-yl]-cyclobutyl ester | 413.5 |
| 303 | Isobutyl-carbamic acid cis-3-[5-(2-m-tolyl-acetylamino)-1H-pyrazol-3-yl]-cyclobutyl ester | 385.4 |
| 304 | Isobutyl-carbamic acid cis-3-{5-[2-(3-methoxy-phenyl)-acetylamino]-1H-pyrazol-3-yl}-cyclobutyl ester | 401.4 |
| 305 | Isobutyl-carbamic acid cis-3-{5-[2-(4-chloro-phenyl)-acetylamino]-1H-pyrazol-3-yl}-cyclobutyl ester | 405.4 |
| 306 | Isobutyl-carbamic acid cis-3-{5-[2-(4-methoxy-phenyl)-acetylamino]-1H-pyrazol-3-yl}-cyclobutyl ester | 401.4 |
| 307 | Isobutyl-carbamic acid cis-3-[5-(2-o-tolyl-acetylamino)-1H-pyrazol-3-yl]-cyclobutyl ester | 385.4 |

| Example | Name | MS (M + H)+ |
|---|---|---|
| 308 | Isobutyl-carbamic acid cis-3-{5-[2-(3-fluoro-phenyl)-acetylamino]-1H-pyrazol-3-yl}-cyclobutyl ester | 389.4 |
| 309 | Isobutyl-carbamic acid cis-3-{5-[2-(3,4-dimethoxy-phenyl)-acetylamino]-1H-pyrazol-3-yl}-cyclobutyl ester | 431.4 |
| 310 | Isobutyl-carbamic acid cis-3-(5-{[1-(4-chloro-phenyl)-cyclopentanecarbonyl]-amino}-1H-pyrazol-3-yl)-cyclobutyl ester | 459.4 |
| 311 | Isobutyl-carbamic acid cis-3-{5-[2-(2-methoxy-phenyl)-acetylamino]-1H-pyrazol-3-yl}-cyclobutyl ester | 401.4 |
| 312 | Isobutyl-carbamic acid cis-3-{5-[2-(3-trifluoromethyl-phenyl)-acetylamino]-1H-pyrazol-3-yl}-cyclobutyl ester | 439.4 |
| 313 | Isobutyl-carbamic acid cis-3-{5-[2-(2-trifluoromethyl-phenyl)-acetylamino]-1H-pyrazol-3-yl}-cyclobutyl ester | 439.4 |
| 314 | Isobutyl-carbamic acid cis-3-{5-[2-(2,6-dichloro-phenyl)-acetylamino]-1H-pyrazol-3-yl}-cyclobutyl ester | 439.3 |
| 315 | Isobutyl-carbamic acid cis-3-{5-[2-(4-isopropyl-phenyl)-acetylamino]-1H-pyrazol-3-yl}-cyclobutyl ester | 413.4 |
| 316 | Isobutyl-carbamic acid cis-3-{5-[2-(2-chloro-4-fluoro-phenyl)-acetylamino]-1H-pyrazol-3-yl}-cyclobutyl ester | 423.3 |
| 317 | Isobutyl-carbamic acid cis-3-{5-[2-(2,4-difluoro-phenyl)-acetylamino]-1H-pyrazol-3-yl}-cyclobutyl ester | 407.4 |
| 318 | Isobutyl-carbamic acid cis-3-{5-[2-(2,6-difluoro-phenyl)-acetylamino]-1H-pyrazol-3-yl}-cyclobutyl ester | 407.4 |
| 319 | Isobutyl-carbamic acid cis-3-{5-[2-(3,4-dichloro-phenyl)-acetylamino]-1H-pyrazol-3-yl}-cyclobutyl ester | 439.3 |
| 320 | Isobutyl-carbamic acid cis-3-{5-[2-(2,5-difluoro-phenyl)-acetylamino]-1H-pyrazol-3-yl}-cyclobutyl ester | 407.4 |
| 321 | Isobutyl-carbamic acid cis-3-{5-[2-(3,4-difluoro-phenyl)-acetylamino]-1H-pyrazol-3-yl}-cyclobutyl ester | 407.4 |
| 322 | Isobutyl-carbamic acid cis-3-[5-(2-benzo[1,3]dioxol-5-yl-acetylamino)-1H-pyrazol-3-yl]-cyclobutyl ester | 415.4 |
| 323 | Isobutyl-carbamic acid cis-3-{5-[2-(4-fluoro-phenyl)-acetylamino]-1H-pyrazol-3-yl}-cyclobutyl ester | 389.4 |
| 324 | Isobutyl-carbamic acid cis-3-(5-phenylacetylamino-1H-pyrazol-3-yl)-cyclobutyl ester | 371.4 |
| 325 | Isobutyl-carbamic acid cis-3-{5-[2-(4-chloro-phenyl)-2-methyl-propionylamino]-1H-pyrazol-3-yl}-cyclobutyl ester | 433.4 |
| 326 | Isobutyl-carbamic acid cis-3-[5-(2,3-diphenyl-propionylamino)-1H-pyrazol-3-yl]-cyclobutyl ester | 461.5 |
| 327 | Isobutyl-carbamic acid cis-3-{5-[2-(3,5-bis-trifluoromethyl-phenyl)-acetylamino]-1H-pyrazol-3-yl}-cyclobutyl ester | 507.5 |
| 328 | Isobutyl-carbamic acid cis-3-{5-[2-(2,4,5-trifluoro-phenyl)-acetylamino]-1H-pyrazol-3-yl}-cyclobutyl ester | 425.4 |
| 329 | Isobutyl-carbamic acid cis-3-{5-[2-(4-methoxy-3-methyl-phenyl)-acetylamino]-1H-pyrazol-3-yl}-cyclobutyl ester | 415.5 |
| 330 | Isobutyl-carbamic acid cis-3-(5-{[1-(4-fluoro-phenyl)-cyclopentanecarbonyl]-amino}-1H-pyrazol-3-yl)-cyclobutyl ester | 443.5 |
| 331 | Isobutyl-carbamic acid cis-3-(5-phenylacetylamino-2H-pyrazol-3-yl)-cyclobutyl ester | 371.4 |
| 332 | Isobutyl-carbamic acid cis-3-{5-[2-(3-chloro-phenyl)-acetylamino]-2H-pyrazol-3-yl}-cyclobutyl ester | 405.1 |
| 333 | Isobutyl-carbamic acid cis-3-{5-[2-(4-bromo-phenyl)-acetylamino]-2H-pyrazol-3-yl}-cyclobutyl ester | 449.1 |
| 334 | Isobutyl-carbamic acid cis-3-[5-(3-methyl-2-phenyl-pentanoylamino)-2H-pyrazol-3-yl]-cyclobutyl ester | 427.5 |
| 335 | Isobutyl-carbamic acid cis-3-{5-[2-(2,4-dichloro-phenyl)-acetylamino]-2H-pyrazol-3-yl}-cyclobutyl ester | 439.3 |
| 336 | Isobutyl-carbamic acid cis-3-(5-{[1-(4-chloro-phenyl)-cyclopropanecarbonyl]-amino}-2H-pyrazol-3-yl)-cyclobutyl ester | 431.3 |
| 337 | Isobutyl-carbamic acid cis-3-{5-[2-(3,5-difluoro-phenyl)-acetylamino]-2H-pyrazol-3-yl}-cyclobutyl ester | 407.4 |
| 338 | Isobutyl-carbamic acid cis-3-[5-(2-benzo[1,3]dioxol-5-yl-acetylamino)-2H-pyrazol-3-yl]-cyclobutyl ester | 415.5 |
| 339 | Isobutyl-carbamic acid cis-3-[5-(2-p-tolyl-acetylamino)-2H-pyrazol-3-yl]-cyclobutyl ester | 385.4 |
| 340 | Isobutyl-carbamic acid cis-3-{5-[2-(2-bromo-5-chloro-phenyl)-acetylamino]-2H-pyrazol-3-yl}-cyclobutyl ester | 485.2 |
| 341 | Isobutyl-carbamic acid cis-3-[5-(2-isochroman-7-yl-acetylamino)-2H-pyrazol-3-yl]-cyclobutyl ester | 427.5 |
| 342 | Isobutyl-carbamic acid cis-3-{5-[2-(2-chloro-6-fluoro-phenyl)-acetylamino]-2H-pyrazol-3-yl}-cyclobutyl ester | 423.9 |
| 343 | Isobutyl-carbamic acid cis-3-{5-[2-(3-acetyl-phenyl)-acetylamino]-2H-pyrazol-3-yl}-cyclobutyl ester | 413.3 |

EXAMPLE 344

Cyclobutyl-carbamic acid cis-3-[5-(3-pyridin-3-yl-propionylamino)-1H-pyrazol-3-yl]-cyclobutyl ester Step A A solution of cyclobutyl-carbamic acid cis-3-(5-amino-1-tert-butyl-1H-pyrazol-3-yl)-cyclobutyl ester (100 mg, prepared by procedures analogous to those described in Example 301, Steps A to C, using appropriate starting materials), 1-propanephosphonic acid cyclic anhydride (50 wt. % in EtOAc, 407 mg), and 3-pyridin-3-yl-propionic acid (60 mg) in EtOAc (2 mL) was heated at reflux overnight. The mixture was concentrated and the residue was used without purification in the next step.

Step B

A solution of the product of Step A in TFA (4 mL) was heated at 80° C. overnight. The solution was then concentrated and the residue was purified by reversed-phase preparative HPLC to afford the title product. MS (M+H)+=384.4.

The following compounds were prepared in a manner analogous to that described in Example 344 using appropriate starting materials. For Examples 345 to 350 and Examples 352 to 368, Et$_3$SiH (3 equivalents) was added to the reaction mixture in Step B.

| Example | Name | MS (M + H)+ |
|---|---|---|
| 345 | Cyclopentyl-carbamic acid cis-3-{5-[3-(4-methyl-thiazol-5-yl)-propionylamino]-1H-pyrazol-3-yl}-cyclobutyl ester | 418.4 |
| 346 | Cyclopentyl-carbamic acid cis-3-{5-[3-(1-methyl-1H-pyrazol-4-yl)-propionylamino]-1H-pyrazol-3-yl}-cyclobutyl ester | 401.5 |
| 347 | Cyclopentyl-carbamic acid cis-3-[5-(3-pyridin-3-yl-propionylamino)-1H-pyrazol-3-yl]-cyclobutyl ester | 398.5 |
| 348 | Pyridin-2-ylmethyl-carbamic acid cis-3-[5-(2,2-dimethyl-propionylamino)-1H-pyrazol-3-yl]-cyclobutyl ester | 372.5 |
| 349 | Pyridin-2-ylmethyl-carbamic acid cis-3-{5-[2-(4-chloro-phenoxy)-2-methyl-propionylamino]-1H-pyrazol-3-yl}-cyclobutyl ester | 484.5 |
| 350 | Pyridin-2-ylmethyl-carbamic acid cis-3-{5-[2-(2-chloro-phenoxy)-acetylamino]-1H-pyrazol-3-yl}-cyclobutyl ester | 456.4 |
| 351 | Pyridin-2-ylmethyl-carbamic acid cis-3-(5-isobutyrylamino-1H-pyrazol-3-yl)-cyclobutyl ester | 358.4 |
| 352 | Pyridin-2-ylmethyl-carbamic acid cis-3-[5-(3,3-dimethyl-butyrylamino)-1H-pyrazol-3-yl]-cyclobutyl ester | 386.5 |
| 353 | Pyridin-2-ylmethyl-carbamic acid cis-3-[5-(3-methyl-butyrylamino)-1H-pyrazol-3-yl]-cyclobutyl ester | 372.5 |
| 354 | Pyridin-2-ylmethyl-carbamic acid cis-3-[5-(cyclopentanecarbonyl-amino)-1H-pyrazol-3-yl]-cyclobutyl ester | 384.5 |
| 355 | Pyridin-2-ylmethyl-carbamic acid cis-3-[5-(cycloheptanecarbonyl-amino)-1H-pyrazol-3-yl]-cyclobutyl ester | 412.5 |
| 356 | Methyl-carbamic acid cis-3-[5-(3-phenyl-propionylamino)-1H-pyrazol-3-yl]-cyclobutyl ester | 343.4 |
| 357 | Dimethyl-carbamic acid cis-3-[5-(3-phenyl-propionylamino)-1H-pyrazol-3-yl]-cyclobutyl ester | 357.4 |
| 358 | Methyl-carbamic acid cis-3-{5-[2-(2-chloro-phenoxy)-acetylamino]-1H-pyrazol-3-yl}-cyclobutyl ester | 379.4 |
| 359 | Dimethyl-carbamic acid cis-3-{5-[2-(2-chloro-phenoxy)-acetylamino]-1H-pyrazol-3-yl}-cyclobutyl ester | 393.4 |
| 360 | Methyl-carbamic acid cis-3-[5-(2-phenoxy-acetylamino)-1H-pyrazol-3-yl]-cyclobutyl ester | 345.3 |
| 361 | Dimethyl-carbamic acid cis-3-[5-(2-phenoxy-acetylamino)-1H-pyrazol-3-yl]-cyclobutyl ester | 359.4 |
| 362 | Dimethyl-carbamic acid cis-3-[5-(2,2-dimethyl-propionylamino)-1H-pyrazol-3-yl]-cyclobutyl ester | 309.4 |
| 363 | Pyridin-2-ylmethyl-carbamic acid cis-3-{5-[(pyridine-2-carbonyl)-amino]-1H-pyrazol-3-yl}-cyclobutyl ester | 393.4 |
| 364 | Pyridin-2-ylmethyl-carbamic acid cis-3-{5-[((S)-tetrahydro-furan-2-carbonyl)-amino]-1H-pyrazol-3-yl}-cyclobutyl ester | 386.2 |
| 365 | Pyridin-2-ylmethyl-carbamic acid cis-3-{5-[2-(4-chloro-phenyl)-2-methyl-propionylamino]-1H-pyrazol-3-yl}-cyclobutyl ester | 468.2 |
| 366 | Pyridin-2-ylmethyl-carbamic acid cis-3-{5-[(5-methyl-pyrazine-2-carbonyl)-amino]-1H-pyrazol-3-yl}-cyclobutyl ester | 408.3 |
| 367 | Pyridin-2-ylmethyl-carbamic acid cis-3-[5-(2-pyridin-2-yl-propionylamino)-2H-pyrazol-3-yl]-cyclobutyl ester | 421.1 |
| 368 | Dimethyl-carbamic acid cis-3-[5-(3-cyclohexyl-propionylamino)-2H-pyrazol-3-yl]-cyclobutyl ester | 363.2 |
| 369 | Cyclobutyl-carbamic acid cis-3-{5-[(tetrahydro-furan-2-carbonyl)-amino]-1H-pyrazol-3-yl}-cyclobutyl ester | 349.4 |

EXAMPLE 370

Cyclobutyl-carbamic acid cis-3-[5-(2,2-dimethyl-propionylamino-1H-pyrazol-3-yl]-cyclobutyl ester Step A A solution of cyclobutyl-carbamic acid cis-3-(5-amino-1-tert-butyl-1H-pyrazol-3-yl)-cyclobutyl ester (100 mg, prepared by procedures analogous to those described in Example 301, Steps A to C, using appropriate starting materials), trimethylacetyl chloride (46 mg), and Et$_3$N (50 mg) in CH$_2$Cl$_2$ was stirred overnight at room temperature. The solution was concentrated to afford a residue that was used without further purification.

Step B

A solution of the product of Step A in TFA (4 mL) was heated at 80° C. overnight. The solution was concentrated and the residue purified by reversed-phase preparative HPLC to afford the title product. MS (M+H)+=335.4

The following compounds were prepared in a manner analogous to that described in Example 370 using appropriate starting materials. For Examples 373 to 377, Et$_3$SiH (3 equivalents) was added to the reaction mixture in Step B.

| Example | Name | MS (M + H)+ |
|---|---|---|
| 371 | Methyl-carbamic acid cis-3-[5-(2,2-dimethyl-propionylamino)-1H-pyrazol-3-yl]-cyclobutyl ester | 295.4 |
| 372 | Dimethyl-carbamic acid cis-3-{5-[(1-phenyl-cyclopentanecarbonyl)-amino]-2H-pyrazol-3-yl}-cyclobutyl ester | 397.2 |
| 373 | Dimethyl-carbamic acid cis-3-[5-(2-methyl-2-phenyl-propionylamino)-2H-pyrazol-3-yl]-cyclobutyl ester | 371.2 |
| 374 | Dimethyl-carbamic acid cis-3-(5-{[1-(4-chloro-phenyl)-cyclobutanecarbonyl]-amino}-2H-pyrazol-3-yl)-cyclobutyl ester | 417.2 |
| 375 | Dimethyl-carbamic acid cis-3-{5-[2-(2-chloro-phenoxy)-2-methyl-propionylamino]-2H-pyrazol-3-yl}-cyclobutyl ester | 421.1 |
| 376 | Dimethyl-carbamic acid cis-3-{5-[2-(4-chloro-phenoxy)-2-methyl-propionylamino]-2H-pyrazol-3-yl}-cyclobutyl ester | 421.1 |
| 377 | Dimethyl-carbamic acid cis-3-[5-(2,2-dimethyl-pentanoylamino)-2H-pyrazol-3-yl]-cyclobutyl ester | 337.2 |

The invention claimed is:
1. A compound of formula (I)

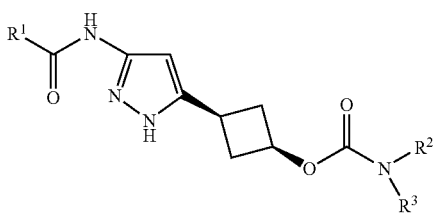

or a pharmaceutically acceptable salt of said compound wherein:

$R^1$ is:
- (A) —($C_1$-$C_6$)alkyl, optionally substituted independently with from one to three (a) halogen; (b) heteroaryl, optionally substituted independently with from one to three —($C_1$-$C_6$)alkyl; trifluoromethyl; or —($C_1$-$C_6$)alkoxy; (c) aryl, optionally substituted independently with from one to three halogen; —($C_1$-$C_6$)alkoxy; trifluoromethyl; —($C_1$-$C_6$)alkyl; or —C(O)($C_1$-$C_6$)alkyl; (d) —$OR^5$; (e) —($C_3$-$C_8$)cycloalkyl; or (f) heterocycloalkyl;
- (B) —($C_3$-$C_8$)cycloalkyl, optionally substituted independently with from one to three (g) heteroaryl, optionally substituted independently with from one to three —($C_1$-$C_6$)alkyl; trifluoromethyl; or —($C_1$-$C_6$)alkoxy; (h) aryl, optionally substituted independently with from one to three halogen; —($C_1$-$C_6$)alkoxy; trifluoromethyl; —($C_1$-$C_6$)alkyl; or —C(O)($C_1$-$C_6$)alkyl; (i) heterocycloalkyl; (j) —$OR^5$; or (k) —($C_1$-$C_6$)alkyl, optionally substituted with from one to three halogen;
- (C) heterocycloalkyl, optionally substituted with from one to three (l) heteroaryl, optionally substituted independently with from one to three —($C_1$-$C_6$)alkyl; trifluoromethyl; or —($C_1$-$C_6$)alkoxy; (m) aryl, optionally substituted independently with from one to three halogen; —($C_1$-$C_6$)alkoxy; trifluoromethyl; —($C_1$-$C_6$)alkyl; or —C(O)($C_1$-$C_6$)alkyl; (n) —($C_3$-$C_8$)cycloalkyl; (o) heterocycloalkyl; (p) —$OR^5$; or (q) —($C_1$-$C_6$)alkyl, optionally substituted with from one to three halogen; or
- (D) heteroaryl, optionally substituted with from one to three —($C_1$-$C_6$)alkyl or trifluoromethyl;

$R^2$ and $R^3$ are, independently,
- (E) hydrogen;
- (F) —($C_1$-$C_6$)alkyl, optionally substituted independently with from one to three (r) halogen; (s) aryl, optionally substituted independently with from one to three halogen; trifluoromethyl; —($C_1$-$C_6$)alkyl, or —($C_1$-$C_6$)alkoxy, optionally substituted with from one to three fluorine atoms; (t) heteroaryl, optionally substituted independently with from one to three nitro; —($C_1$-$C_6$)alkyl; trifluoromethyl; halogen; or —($C_1$-$C_6$)alkoxy; (u) heterocycloalkyl, optionally substituted independently with one to three —($C_1$-$C_6$)alkyl; oxo; aryl; or heteroaryl; (v) —($C_3$-$C_8$)cycloalkyl, optionally substituted independently with from one to three cyano or aryl; (w) —$NHR^4$; (x) —$OR^5$; (y) —N[($C_1$-$C_6$)alkyl]$_2$; or (z) cyano;
- (G) —($C_3$-$C_8$)cycloalkyl, optionally substituted independently with from one to three cyano or aryl;
- (H) aryl, optionally substituted independently with from one to three halogen; —($C_1$-$C_6$)alkoxy; trifluoromethyl; or —($C_1$-$C_6$)alkyl;
- (I) heteroaryl, optionally substituted independently with from one to three —($C_1$-$C_6$)alkyl or —($C_1$-$C_6$)alkoxy; or
- (J) heterocycloalkyl, optionally substituted with from one to three —($C_1$-$C_6$)alkyl, optionally substituted with aryl; or $R^2$ and $R^3$, taken together with the nitrogen atom to which they are attached, form a heterocycloalkyl ring, optionally substituted independently with (aa) —($C_1$-$C_6$)alkyl, optionally substituted with —$R^4$ or —$OR^5$; (bb) aryl; (cc) heteroaryl; (dd) —N[($C_1$-$C_6$)alkyl]$R^4$; (ee) —$R^4$; or (ff) —($C_1$-$C_6$)alkoxy;

$R^4$ is (K) —($C_1$-$C_6$)alkyl; (L) —C(O)($C_1$-$C_6$)alkyl; (M) —C(O)O($C_1$-$C_6$)alkyl, optionally substituted with aryl; (N) aryl; (O) heteroaryl; or (P) heterocycloalkyl, wherein each (N) aryl, (O) heteroaryl, or (P) heterocycloalkyl group is optionally substituted independently with from one to three (gg) halogen; (hh) nitro; (ii) trifluoromethyl; (jj) —($C_1$-$C_6$)alkyl; or (kk) —N[($C_1$-$C_6$)alkyl][C(O)($C_1$-$C_6$)alkyl]; and $R^5$ is (Q) —($C_1$-$C_6$)alkyl; (R) —C(O)($C_1$-$C_6$)alkyl; (S) aryl; (T) heteroaryl; or (U) heterocycloalkyl, wherein each (S) aryl, (T) heteroaryl, or (U) heterocycloalkyl group is optionally substituted independently with from one to three (ll) halogen; (mm) nitro; (nn) trifluoromethyl; (oo) —($C_1$-$C_6$)alkyl; or (pp) —N[($C_1$-$C_6$)alkyl][C(O)($C_1$-$C_6$)alkyl].

2. A compound of claim 1, wherein:

$R^1$ is:
- (A) —($C_1$-$C_6$)alkyl, optionally substituted independently with (b) heteroaryl, optionally substituted independently with —($C_1$-$C_6$)alkyl; trifluoromethyl; or —($C_1$-$C_6$)alkoxy; (c) aryl, optionally substituted independently with from one to three halogen; —($C_1$-$C_6$)alkoxy; trifluoromethyl; —($C_1$-$C_6$)alkyl; (d) —$OR^5$; or (f) heterocycloalkyl;
- (B) —($C_3$-$C_8$)cycloalkyl, optionally substituted independently with (g) heteroaryl, optionally substituted independently with from one to three —($C_1$-$C_6$)alkyl; trifluoromethyl; or —($C_1$-$C_6$)alkoxy; (h) aryl, optionally substituted independently with from one to three halogen; —($C_1$-$C_6$)alkoxy; trifluoromethyl; or —($C_1$-$C_6$)alkyl; (i) heterocycloalkyl; (j) —$OR^5$; (k) —($C_1$-$C_6$)alkyl, optionally substituted with from one to three halogen;
- (C) heterocycloalkyl, optionally substituted with (l) heteroaryl, optionally substituted independently with from one to three —($C_1$-$C_6$)alkyl; trifluoromethyl; or —($C_1$-$C_6$)alkoxy; (m) aryl, optionally substituted independently with from one to three halogen; —($C_1$-$C_6$)alkoxy; trifluoromethyl; —($C_1$-$C_6$)alkyl; or —C(O)($C_1$-$C_6$)alkyl; (n) —($C_3$-$C_8$)cycloalkyl; (o) heterocycloalkyl; (p) —$OR^5$; or (q) —($C_1$-$C_6$)alkyl, optionally substituted with from one to three halogen;

$R^2$ is hydrogen or —($C_1$-$C_6$)alkyl;

$R^3$ is:
- (F) —($C_1$-$C_6$)alkyl, optionally substituted independently with from one to three (r) halogen; (s) aryl, optionally substituted independently with from one to three halogen; trifluoromethyl; —($C_1$-$C_6$)alkyl, or —($C_1$-$C_6$)alkoxy, optionally substituted with from one to three fluorine atoms; (t) heteroaryl, optionally substituted independently with from one to three —($C_1$-$C_6$)alkyl; trifluoromethyl; halogen; or —($C_1$-$C_6$)alkoxy; (u) heterocycloalkyl, optionally substituted independently with one to three —($C_1$-$C_6$)alkyl; oxo; aryl; or heteroaryl; (v) —(C$_3$-C$_8$)cycloalkyl; (w) —NHR$^4$; (x) —OR$^5$; (y) —N[(C$_1$-C$_6$)alkyl]$_2$; or (z) cyano;
(G) —(C$_3$-C$_8$)cycloalkyl, optionally substituted independently with from one to three cyano or aryl; or
(J) heterocycloalkyl, optionally substituted with from one to three —(C$_1$-C$_6$)alkyl, optionally substituted with aryl; or R$^2$ and R$^3$, taken together with the nitrogen atom to which they are attached, form a heterocycloalkyl ring, optionally substituted independently with (aa) —(C$_1$-C$_6$)alkyl, optionally substituted with —R$^4$ or —OR$^5$; (bb) aryl; (cc) heteroaryl; or (ff) —(C$_1$-C$_6$)alkoxy;

R$^4$ is (K) —(C$_1$-C$_6$)alkyl; (N) aryl; (O) heteroaryl; or (P) heterocycloalkyl, wherein each aryl, heteroaryl, or heterocycloalkyl group is optionally substituted independently with from one to three (gg) halogen; (ii) trifluoromethyl; or (jj) —(C$_1$-C$_6$)alkyl; and R$^5$ is (Q) —(C$_1$-C$_6$)alkyl; (S) aryl; (T) heteroaryl; or (U) heterocycloalkyl, wherein each (S) aryl, (T) heteroaryl, or (U) heterocycloalkyl group is optionally substituted independently with from one to three (ll) halogen; (nn) trifluoromethyl; or (oo) —(C$_1$-C$_6$)alkyl.

3. A compound of claim 1, wherein:
R$^1$ is:
(A) —(C$_1$-C$_6$)alkyl, optionally substituted independently with (b) heteroaryl, optionally substituted independently with —(C$_1$-C$_6$)alkyl or —(C$_1$-C$_6$)alkoxy; (c) aryl, optionally substituted independently with from one to three halogen; —(C$_1$-C$_6$)alkoxy; trifluoromethyl; or —(C$_1$-C$_6$)alkyl; or (d) —OR$^5$;
(B) —(C$_3$-C$_8$)cycloalkyl, optionally substituted independently with (g) heteroaryl, optionally substituted independently with from one to three —(C$_1$-C$_6$)alkyl or —(C$_1$-C$_6$)alkoxy; (h) aryl, optionally substituted independently with from one to three halogen; —(C$_1$-C$_6$) alkoxy; trifluoromethyl; or —(C$_1$-C$_6$)alkyl; (j) —OR$^5$; (k) —(C$_1$-C$_6$)alkyl, optionally substituted with from one to three halogen; or
(C) heterocycloalkyl, optionally substituted with (l) heteroaryl, optionally substituted independently with from one to three —(C$_1$-C$_6$)alkyl or —(C$_1$-C$_6$)alkoxy; (m) aryl, optionally substituted independently with from one to three halogen; —(C$_1$-C$_6$)alkoxy; trifluoromethyl; or —(C$_1$-C$_6$)alkyl; (p) —OR$^5$; or (q) —(C$_1$-C$_6$)alkyl, optionally substituted with from one to three halogen;

R$^2$ is hydrogen or —(C$_1$-C$_6$)alkyl;
R$^3$ is:
(F) —(C$_1$-C$_6$)alkyl, optionally substituted independently with (s) aryl, optionally substituted independently with from one to three halogen; trifluoromethyl; —(C$_1$-C$_6$) alkyl, or —(C$_1$-C$_6$)alkoxy, optionally substituted with from one to three fluorine atoms; (t) heteroaryl, optionally substituted independently with from one to three —(C$_1$-C$_6$)alkyl or trifluoromethyl; and
R$^5$ is (S) aryl, optionally substituted with halogen.

4. The compound:
benzyl-carbamic acid cis-3-[5-(cyclohexanecarbonyl-amino)-1H-pyrazol-3-yl]-cyclobutyl ester;
benzyl-carbamic acid cis-3-(5-isobutyrylamino-1H-pyrazol-3-yl)-cyclobutyl ester;
benzyl-carbamic acid cis-3-[5-(2-methyl-2-phenyl-propionylamino)-2H-pyrazol-3-yl]-cyclobutyl ester;
benzyl-carbamic acid cis-3-{5-[(4-methyl-tetrahydro-pyran-4-carbonyl)-amino]-2H-pyrazol-3-yl}-cyclobutyl ester;
benzyl-carbamic acid cis-3-[5-(2,2-dimethyl-propionylamino)-2H-pyrazol-3-yl]-cyclobutyl ester;
benzyl-carbamic acid cis-3-{5-[(tetrahydro-pyran-4-carbonyl)-amino]-1H-pyrazol-3-yl}-cyclobutyl ester;
benzyl-carbamic acid cis-3-[5-(2-methyl-2-pyridin-2-yl-propionylamino)-2H-pyrazol-3-yl]-cyclobutyl ester;
benzyl-methyl-carbamic acid cis-3-{5-[(tetrahydro-pyran-4-carbonyl)-amino]-1H-pyrazol-3-yl}-cyclobutyl ester;
butyl-carbamic acid cis-3-[5-(2,2-dimethyl-propionylamino)-1H-pyrazol-3-yl]-cyclobutyl ester;
(2-chloro-benzyl)-carbamic acid cis-3-{5-[(tetrahydro-pyran-4-carbonyl)-amino]-1H-pyrazol-3-yl}-cyclobutyl ester;
(2,6-difluoro-benzyl)-carbamic acid cis-3-(5-isobutyrylamino-2H-pyrazol-3-yl)-cyclobutyl ester;
(2,6-difluoro-benzyl)-carbamic acid cis-3-{5-[(1-methyl-cyclohexanecarbonyl)-amino]-1H-pyrazol-3-yl}-cyclobutyl ester; p1 (2-ethyl-butyl)-carbamic acid cis-3-(5-isobutyrylamino-2H-pyrazol-3-yl)-cyclobutyl ester;
(2-fluoro-benzyl)-carbamic acid cis-3-{5-[((R)-tetrahydro-furan-2-carbonyl)-amino]-1H-pyrazol-3-yl}-cyclobutyl ester;
isobutyl-carbamic acid cis-3-(5-phenylacetylamino-2H-pyrazol-3-yl)-cyclobutyl ester;
(2-phenyl-propyl)-carbamic acid cis-3-(5-[((R)-tetrahydro-furan-2-carbonyl)-amino]-1H-pyrazol-3-yl)-cyclobutyl ester;
pyridin-2-ylmethyl-carbamic acid cis-3-[5-(cyclopentanecarbonyl-amino)-1H-pyrazol-3-yl]-cyclobutyl ester;
pyridin-2-ylmethyl-carbamic acid cis-3-[5-(2,2-dimethyl-propionylamino)-1H-pyrazol-3-yl]-cyclobutyl ester;
thiophen-2-ylmethyl-carbamic acid cis-3-{5-[((R)-tetrahydro-furan-2-carbonyl)-amino]-1H-pyrazol-3-yl}-cyclobutyl ester; or
(2-trifluoromethyl-benzyl)-carbamic acid cis-3-(5-isobutyrylamino-2H-pyrazol-3-yl)-cyclobutyl ester; or a pharmaceutically acceptable salt of said compound.

5. A pharmaceutical composition comprising an amount of a compound of claim 1, or a pharmaceutically acceptable salt of said compound, and a pharmaceutically acceptable carrier, vehicle, or diluent.

6. A pharmaceutical composition comprising an amount of a compound of claim 1, or a pharmaceutically acceptable salt of said compound; an amount of one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), or (xii) a potassium channel modulator; and a pharmaceutically acceptable carrier, vehicle, or diluent.

7. A compound selected from the group consisting of:
(3-Chloro-benzyl)-carbamic acid cis-3-{5-[(tetrahydro-pyran-4-carbonyl )-amino ]-1H-pyrazol-3-yl}-cyclobutyl ester;
Benzyl-carbamic acid cis-3-{5-[((R)-tetrahydro-furan-2-carbonyl)-amino]-1H-pyrazol-3-yl}-cyclobutyl ester;
Pyridin-2-ylmethyl-carbamic acid cis-3-[5-(2,2-dimethyl-propionylamino)-1H-pyrazol-3-yl]-cyclobutyl ester;
Pyridin-2-ylmethyl-carbamic acid cis-3-[5-(cycloheptanecarbonyl-amino)-1H-pyrazol-3-yl]-cyclobutyl ester;
(3-Chloro-benzyl)-carbamic acid cis-3-{5-[((R)-tetrahydro-furan-2-carbonyl)-amino ]-1 H-pyrazol-3-yl}-cyclobutyl ester;
(2-Phenyl-propyl)-carbamic acid cis-3-{5-[((R)-tetrahydro-furan-2-carbonyl)-amino ]-1 H-pyrazol-3-yl}-cyclobutyl ester;

(2-Chloro-6-fluoro-benzyl)-carbamic acid cis-3-{5-[((R)-tetrahydro-furan-2-carbonyl)-amino ]-2H-pyrazol-3-yl}-cyclobutyl ester;

(2,3-Difluoro-benzyl)-carbamic acid cis-3-{5-[((R)-tetrahydro-furan-2-carbonyl)-amino ]-2H-pyrazol-3-yl}-cyclobutyl ester;

(2,6-Difluoro-benzyl)-carbamic acid cis-3-{5-[((R)-tetrahydro-furan-2-carbonyl)-amino ]-2H-pyrazol-3-yl}-cyclobutyl ester;

(2-Methoxy-benzyl)-carbamic acid cis-3-{5-[((R)-tetrahydro-furan-2-carbonyl )-amino ]-1H-pyrazol-3-yl}-cyclobutyl ester;

(2-Fluoro-6-trifluoromethyl-benzyl)-carbamic acid cis-3-{5-[((R)-tetrahydro-furan-2-carbonyl)-amino ]-1H-pyrazol-3-yl}-cyclobutyl ester;

(2-Chloro-6-fluoro-benzyl)-carbamic acid cis-3-{5-[(tetrahydro-pyran-4-carbonyl)-amino ]-2H-pyrazol-3-yl}-cyclobutyl ester;

(4-Fluoro-2-trifluoromethyl-benzyl)-carbamic acid cis-3-{5-[((R)-tetrahydro-furan-2-carbonyl)-amino ]-2H-pyrazol-3-yl}-cyclobutyl ester;

(3-Fluoro-benzyl)-carbamic acid cis-3-{5-[(1 -methyl-cyclohexanecarbonyl)-amino]-1H-pyrazol-3-yl}-cyclobutyl ester;

(1-Methyl-1-phenyl-ethyl)-carbamic acid cis-3-{5-[(tetrahydro-pyran-4-carbonyl)-amino ]-2H-pyrazol-3-yl}-cyclobutyl ester;

(2-Methyl-benzyl)-carbamic acid cis-3-[5-(2-methyl-2-phenyl-propionylamino)-2H-pyrazol-3-yl]-cyclobutyl ester;

(1-Methyl-1-phenyl-ethyl)-carbamic acid cis-3-[5-(2-methyl-2-pyridin-2-yl-propionylamino)-2H-pyrazol-3-yl]-cyclobutyl ester;

(2-Trifluoromethyl-benzyl)-carbamic acid cis-3-[5-(2-methyl-2-phenyl-propionylamino)-2H-pyrazol-3-yl]-cyclobutyl ester;

(2-Fluoro-benzyl)-carbamic acid cis-3-[5-(2-methyl-2-phenyl-propionylamino)-2H-pyrazol-3-yl]-cyclobutyl ester;

(2-Methoxy-benzyl)-carbamic acid cis-3-[5-(2-methyl-2-phenyl-propionylamino)-2H-pyrazol-3-yl]-cyclobutyl ester;

(1-Phenyl-cyclopentyl)-carbamic acid cis-3-[5-(2,2-dimethyl-propionylamino)-2H-pyrazol-3-yl]-cyclobutyl ester;

Pyridin-2-ylmethyl-carbamic acid cis-3-[5-(2-pyridin-2-yl-propionylamino)-2H-pyrazol-3-yl]-cyclobutyl ester;

(2-Phenylamino-ethyl)-carbamic acid cis-3-(5-isobutyrylamino-2H-pyrazol-3-yl)-cyclobutyl ester;

(4-Chloro-benzyl)-carbamic acid cis-3-(5-isobutyrylamino-2H-pyrazol-3-yl)-cyclobutyl ester;

(2-Chloro-6-fluoro-benzyl)-carbamic acid cis-3-(5-isobutyrylamino-2H-pyrazol-3-yl)-cyclobutyl ester;

(2,4,5-Trifluoro-benzyl)-carbamic acid cis-3-{5-[((R)-tetrahydro-furan-2-carbonyl )-amino ]-2H-pyrazol-3-yl}-cyclobutyl ester;

(3,4-Difluoro-benzyl)-carbamic acid cis-3-{5-[((R)-tetrahydro-furan-2-carbonyl)-amino ]-2H-pyrazol-3-yl}-cyclobutyl ester;

(2-Methyl-benzyl)-carbamic acid cis-3-{5-[(tetrahydro-pyran-4-carbonyl)-amino ]-2H-pyrazol-3-yl}-cyclobutyl ester;

(2,5-Difluoro-benzyl)-carbamic acid cis-3-{5-[((R)-tetrahydro-furan-2-carbonyl)-amino ]-2H-pyrazol-3-yl}-cyclobutyl ester;

(2-Trifluoromethyl-benzyl)-carbamic acid cis-3-{5-[((R)-tetrahydro-furan-2-carbonyl)-amino ]-1H-pyrazol-3-yl}-cyclobutyl ester;

(2-Methyl-benzyl)-carbamic acid cis-3-{5-[((R)-tetrahydro-furan-2-carbonyl )-amino ]-2H-pyrazol-3-yl}-cyclobutyl ester;

(2,4-Difluoro-benzyl)-carbamic acid cis-3-{5-[((R)-tetrahydro-furan-2-carbonyl)-amino ]-2H-pyrazol-3-yl}-cyclobutyl ester;

(4-Isopropyl-benzyl)-carbamic acid cis-3-{5-[((R)-tetrahydro-furan-2-carbonyl)-amino ]-1H-pyrazol-3-yl}-cyclobutyl ester;

(4-Chloro-benzyl)-carbamic acid cis-3-{5-[((R)-tetrahydro-furan-2-carbonyl)-amino ]-1H-pyrazol-3-yl}-cyclobutyl ester;

(2-Chloro-benzyl)-carbamic acid cis-3-{5-[((R)-tetrahydro-furan-2-carbonyl)-amino ]-1H-pyrazol-3-yl}-cyclobutyl ester;

Pyridin-2-ylmethyl-carbamic acid cis-3-[5-(3,3-dimethyl-butyrylamino)-1H-pyrazol-3-yl]-cyclobutyl ester;

Pyridin-2-ylmethyl-carbamic acid cis-3-(5-isobutyrylamino-1H-pyrazol-3-yl)-cyclobutyl ester;

Benzyl-methyl-carbamic acid cis-3-{5-[((R)-tetrahydro-furan-2-carbonyl)-amino ]-1H-pyrazol-3-yl}-cyclobutyl ester;

Pyridin-2-ylmethyl-carbamic acid cis-3-{5-[((R)-tetrahydro-furan-2-carbonyl)-amino ]-1H-pyrazol-3-yl}-cyclobutyl ester;

(2-Methoxy-benzyl)-carbamic acid cis-3-[5-(2,2-dimethyl-propionylamino)-1H-pyrazol-3-yl]-cyclobutyl ester;

(1-Phenyl-propyl)-carbamic acid cis-3-[5-(2,2-dimethyl-propionylamino)-2H-pyrazol-3-yl]-cyclobutyl ester; and ((S)-1-Phenyl-ethyl)-carbamic acid cis-3-[5-(2,2-dimethyl-propionylamino)-2H-pyrazol-3-yl]-cyclobutyl ester;

or a pharmaceutically acceptable salt of said compound.

* * * * *